(12) United States Patent
Cerni et al.

(10) Patent No.: US 6,275,290 B1
(45) Date of Patent: *Aug. 14, 2001

(54) CHEMICAL MECHANICAL PLANARIZATION (CMP) SLURRY QUALITY CONTROL PROCESS AND PARTICLE SIZE DISTRIBUTION MEASURING SYSTEMS

(75) Inventors: Todd A. Cerni, Longmont; Scott Waisanen, Louisville; Dennis J. Knowlton, Boulder, all of CO (US)

(73) Assignee: Particle Measuring Systems, Inc., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/296,928

(22) Filed: Apr. 22, 1999

Related U.S. Application Data

(63) Continuation-in-part of application No. 09/069,682, filed on Apr. 29, 1998.

(51) Int. Cl.[7] ............................................. G01N 15/02
(52) U.S. Cl. ................................................. 356/335
(58) Field of Search .................................. 356/335–343, 356/73, 432–440; 438/455, 515, 800; 73/24.02, 24.03, 61.75; 451/5, 41, 6, 8

(56) References Cited

U.S. PATENT DOCUMENTS

| 4,279,512 | 7/1981 | Tunstall | 356/335 |
|---|---|---|---|
| 4,318,180 | 3/1982 | Lundqvist et al. | 364/555 |
| 4,329,053 | 5/1982 | Fyumat | 356/336 |

(List continued on next page.)

FOREIGN PATENT DOCUMENTS

| 0 564 157 A1 | 6/1993 | (EP) . |
|---|---|---|
| 0 590 841 A1 | 6/1994 | (EP) . |
| 0 654 661 A1 | 5/1995 | (EP) . |
| 2 454 102 | 7/1980 | (FR) . |

OTHER PUBLICATIONS

"Commercial spectrophotomer for particle sizing", Fabio Ferri, Alessandra Bassini, and Enrico Paganini, *Applied Optics*, Feb. 1, 1997, vol. 36, No. 4, pp. 885–891.

(List continued on next page.)

*Primary Examiner*—Hoa Q. Pham
(74) *Attorney, Agent, or Firm*—Patton Boggs LLP

(57) ABSTRACT

A sensitive particle distribution probe uses special processing including a modified Twomey/Chahine iterative convergence technique and a specially constructed sample cell to obtain particle size distribution measurements from optically dense slurries, such as the slurries used in the semiconductor industry for chemical mechanical planarization. Spectral transmission data is taken over the spectral range of 0.20–2.5 microns, utilizing specially constructed, chemically resistant sample cells of 50–2000 microns thickness, and miniature, fixed grating, linear detector array spectrometers. At wavelengths greater than one micron, the preferred design utilizes InGaAs linear detector arrays. An ultrasonic disrupter can be employed to breakup harmless soft agglomerates. In addition to direct particle size distribution measurement, the invention described here could be used to detect other fundamental causes of slurry degradation, such as foaming and jelling. The probe accomplishes continuous, real time sampling of undiluted slurry. A three-position chopper allows automated operation in an industrial environment without the need for frequent reference spectra, which would require taking the probe off-line. In other embodiments, the invention provides a quality control and/ or particle size measuring system for CMP slurries using transmission data through an as-used CMP slurry flow. The process of the invention detects transmission through the flow, at select wavelengths, and determines changes in the logarithmic slope of transmission versus wavelength to detect acceptable or unacceptable CMP slurries. The process can further determine CMP slurry particle size through empirical extinction data stored in memory.

33 Claims, 15 Drawing Sheets

U.S. PATENT DOCUMENTS

| | | | |
|---|---|---|---|
| 4,338,030 | | 7/1982 | Loos .................................... 356/336 |
| 4,373,807 | * | 2/1983 | Gouesbet ........................... 356/28.5 |
| 4,652,755 | | 3/1987 | Solomon et al. .................... 250/341 |
| 4,790,652 | | 12/1988 | Uneus et al. ........................ 356/45 |
| 5,007,297 | | 4/1991 | Sommer ............................. 73/865.5 |
| 5,164,787 | | 11/1992 | Igushi et al. ........................ 356/338 |
| 5,371,020 | | 12/1994 | Frischauf ........................... 436/165 |
| 5,379,113 | * | 1/1995 | Niwa ................................... 356/336 |
| 5,422,712 | * | 6/1995 | Ogino .................................. 356/73 |
| 5,475,486 | | 12/1995 | Paoli ................................... 356/246 |
| 5,485,270 | | 1/1996 | Freud et al. ........................ 356/336 |
| 5,572,321 | * | 11/1996 | Pinier et al. ........................ 356/338 |
| 5,616,457 | | 4/1997 | Garcia-Rubio ..................... 435/4 |
| 5,710,069 | | 1/1998 | Farkas et al. ....................... 438/7 |
| 6,119,510 | * | 9/2000 | Carasso et al. .................... 73/61.75 |

OTHER PUBLICATIONS

"Analysis of particle sizes, concentration, and refractive index in measurement of light transmittance in the forward–scattering–angle range", Anatoil P. Nefedov, Oleg F. Petrov, and Olga S. Vaulina, *Applied Optics*, Feb. 20, 1997, vol. 36, No. 6, pp. 1357–1366.

International Search Report, Jul. 28, 1999, European Patent Office, P.B. 5818 Patentlaan 2, NL–2280 HV Rijswijk.

"Comparison of Constrained Linear Inversion and an Iterative Nonlinear Algorithm Applied to the Indirect Estimation of Particle Size Distributions" by. S. Twomey, *Journal of Computational Physics*, vol. 18, No. 2, Jun. 1975, pp. 188–200.

"Paticle Size Determination Using Turbidimetry, Capabilities, Limitations, and Evalution for On–Line Applications" by Theodora Kourti and John F. MacGregor, *American Chemical Society publication*, 1991, pp. 34–63.

* cited by examiner

CHEMICAL MECHANICAL PLANARIZATION (CMP) SLURRY QUALITY CONTROL PROCESS AND PARTICLE SIZE DISTRIBUTION MEASURING SYSTEMS

RELATED APPLICATIONS

This application is a continuation-in-part of commonly-owned and U.S. application Ser. No. 09/069,682, filed on Apr. 29, 1998, which is incorporated herein by reference.

FIELD OF THE INVENTION

The invention pertains to the field of measurements performed on slurries to determine the slurry particle size distribution. More specifically, the measurements concern a use of instrumentation to determine particle concentration as a function of particle size in substantially opaque slurries, such as chemical mechanical planarization ("CMP") slurries currently used in semiconductor manufacturing. The invention further relates to quality control processes used to improve semiconductor manufacturing processes.

BACKGROUND OF THE INVENTION

CMP processes are used in the semiconductor and optics industries to provide ultra-smooth surfaces. CMP process slurries typically consist of $SiO_2$ or $Al_2O_3$ particles suspended in an acid or base solution at a concentration of 4% to 18% solids by weight. $SiO_2$ slurries are referred to in the art as "oxide" slurries, and $Al_2O_3$ slurries are referred to as "metal" slurries. It is difficult to check the quality the particle size distributions within these slurries due to the sub-micron sizes of the particles and the substantially opaque nature of the slurry.

CMP slurries facilitate the deposition of uniform planarized layers in multiple layer wafers, resulting in ultra-smooth surfaces that enhance the resolution of embedded integrated circuit microfeatures. Particles having dimensions that exceed a delimiting value for a particular application are analogous to sandpaper having grit that is too large, and disadvantageously score or scratch the surface that is being smoothed. Thus, it is an essential quality control process to eliminate the use of slurries having particles that are too large.

The use of CMP slurries in semiconductor manufacturing has risen sharply over the last five years. It has emerged as the preferred method of planarization for manufacture of multiple layer semiconductor wafers having feature sizes less than or equal to 0.35 micron. It has been observed that semiconductor wafers can be scratched and thereby damaged if a significant concentration of large particles appear in the slurry through either contamination or agglomeration. The size threshold for particles that are large enough to damage wafers is believed to be in the range of 0.5–3.0 microns. CMP slurry manufacturers attempt to produce slurries that consist predominantly of particles less than 1.0 or even 0.5 micron in size.

Commercially available sensor devices are presently unable to meet the needs of those who wish to measure the particle size distribution of CMP slurries. It is desirable to perform continuous measurements of the CMP slurry particle size distribution in real-time, in order to eliminate the risk of using slurries having particles or agglomerated particles that are too large. This enhanced process control, if available, would allow early detection and cure of slurry problems. The use of the term "real-time" in this discussion means that the measurement results are available within a few seconds after sampling. It is also desirable to measure the particle size distribution of undiluted slurry because dilution and the subsequent change in pH can alter the distribution. Furthermore, dilution combined with continuous sampling creates large volumes of waste slurry. These needs characterize the present state of the art in measuring and/or detecting the particle size distribution of CMP slurries.

Existing commercial particle size sensors include those based on measurement of angular light scattering, dynamic light scattering or photon correlation spectroscopy, ultrasonic transmission, and capillary hydrodynamic fractionalization. These measurement techniques are problematic because they require (a) substantial dilution of the optically dense CMP slurries, or (b) discontinuous batch sampling of the slurry, or they have insufficient sensitivity to detect small changes in the particle size distribution over the critical size range of 0.5 to 3.0 microns.

The need to dilute CMP slurries for particle size measurements creates large amounts of waste that cannot be recovered into usable CMP slurry. According to the data of Bare et al., *Monitoring slurry stability to reduce process variability*, Micro. Vol. 15, No. 8, pp. 53–63 (1997), oxide slurries typically have $2 \times 10^5/cm^3$ particles greater than one micron, and metal slurries typically have $7 \times 10^8/cm^3$ particles greater than one micron. This data was obtained using a Particle Measurement Systems LiQuilaz SO5 particle size detector, which is specified for a maximum particle concentration of $12,000/cm^3$ to keep coincidence errors less than ten percent. The SO5 detector is typical of commercially available single particle light scattering devices. Thus, a minimum dilution factor of seventeen is required to reduce coincidence errors for oxide slurries, and a minimum dilution factor of 58,350 is required for metal slurries. These dilution factors represent significant amounts of process slurry waste, and the dilution itself is suspected of altering the size distribution through agglomeration.

U.S. Pat. No. 5,710,069 (the '069 patent) to Farkas et al. discusses an optical particle counter that detects only one partide at a time in CMP slurries. The single particle must flow through a sample volume consisting of the intersection of a light beam and a detector field of view. The '069 patent does not discuss the difficulty in requiring the light beam to penetrate the slurry towards the measurement area (sample volume), nor in achieving detection of one particle at a time in slurries which typically contain of $10^{13}$ – $10^{14}$ particles per $cm^3$. The idea of being able to measure only one particle at a time is unsupported by any calculations, numerical arguments, or design details. It is unclear whether the '069 patent uses Mie scattering calculations or empirical correlations to calculate particle size distribution based upon the number of single particles that are counted. The technique of "photocorrelation" is said not to work, but no description is provided of a technique that does work.

U.S. Pat. No. 5,616,457 (the '457 patent) to Garcia-Rubio teaches an apparatus for detecting the presence of a microorganism in a liquid sample. A Twomey linear inversion with a smoothing constraint is used to calculate particle size distribution for the organism. A standard commercial spectrophotometer having a one centimeter cell path length is used to perform the measurements. Additional detail regarding the Twomey linear inversion can be found in Twomey, *Comparison of Constrained Linear Inversion and an Iterative Nonlinear Algorithm Applied to the Indirect Estimation of Particle Size Distributions*, J. Comp. Phys. Vol. 18, No. 2, 188–200 (1975). The '457 patent does not require dilution because it addresses solutions that are much less optically dense than CMP slurries.

Examples of the present state of the art in measuring particle size distribution in optically dense mixtures of sub-micron particles suspended in a liquid solution include two presentations at a recent American Chemical Society symposium: Kourti et al., *Particle Size Determination Using Turbidimetry*, Particle Size Distribution II—Assessment and Characterization, pp. 35–63, Amer. Chem. Soc. Symposium No. 472 (1991); and Brandolin et al., *On-line Particle Size Distribution Measurements for Latex Reactors*, Particle Size Distribution II—Assessment and Characterization, pp. 65–85 (1991). These authors typically utilize measurements at two to three wavelengths in the range of 0.2–1.0 microns. Conventional sample cells on the order of one centimeter in thickness were apparently utilized. The limited wavelength range and conventional sample cell dimensions force significant sample dilution, which in turn results in generation of a large waste stream of diluted product. An off-line batch sampling system may also be used, but this type of system has an unacceptably slow time response.

There remains a need for a real-time probe for use in obtaining continuous particle size distribution measurements that do not require dilution of the CMP slurry. The probe should retrieve particle distribution over a broad range of sizes, and consistently detect small changes in the particle size distribution, while providing autonomous operation in an industrial environment.

There is the further need to detect changes in the particle size distribution of a CMP slurry as a quality control process.

It is, accordingly, one object of the invention to provide a probe and/or system which provides real-time measurement of CMP slurry particle size distributions and/or change of the particle size distribution. Another object of the invention is to provide a quality control process to detect acceptable and unacceptable CMP slurries, real-time, in a manufacturing environment. Yet another object of the invention is to provide systems and methods for detecting CMP slurry particle size distributions and/or changes in such distributions. These and other objects of the invention are apparent within the description which follows.

SUMMARY OF THE INVENTION

The following patents provide useful background information for the invention and relating to turbo pumps: U.S. Pat. No. 3,832,084; U.S. Pat. No. 3,969,042; U.S. Pat. No. 4,929,151; U.S. Pat. No. 4,893,985; U.S. Pat. No. 4,764,034; U.S. Pat. No. 4,734,018; U.S. Pat. No. 3,753,623; U.S. Pat. No. 3,947,193; U.S. Pat. No. 5,451,147; and U.S. Pat. No. 4,180,370. Each of the afore-mentioned patents is incorporated herein by reference.

The present invention overcomes the problems outlined above, and advances the art, by providing real-time systems, methods and/or probes for continuous particle size distribution measurement and/or quality control of undiluted CMP slurry. The CMP slurry can include a broad range of particle sizes, e.g., from 0.03 $\mu$m to over 1.0 $\mu$m diameter particles. The systems and methods of the invention provide high sensitivity to small changes in physical and/or chemical characteristics of the CMP slurry (e.g., to detect changes in the particle size distribution of the CMP slurry), and preferably with autonomous operation in an industrial environment. These advantages are obtained, in certain aspects, by measuring spectral transmission through undiluted CMP slurry samples (typically through a slurry "flow"). The spectral transmission measurements are made at one or more wavelengths, and preferably at two or more wavelengths. The slurry flow typically moves through sample cells having widths as narrow as 50microns, though typically the width is 100 microns or more. CMP slurries have high optical extinction per unit length in the visible spectrum by virtue of the high particle concentration and sub-micron particle sizes. A reasonable fraction of the incident light beam, i.e., an amount greater than approximately 5%, must penetrate the sample, without being scattered, in order to obtain useful spectral transmission data. This goal is accomplished, in one aspect, by extending the spectral transmission measurements to approximately 2.5 microns in wavelength, which is well beyond the 1.0 micron limit used in the prior art, and by utilizing specially constructed sample cells having a path length of 50–2000 microns. In another aspect, a spectral wavelength range of 0.20–2.5 microns is used to retrieve the CMP slurry particle size distribution of CMP slurries used in semiconductor manufacturing.

In one aspect, a probe according to the invention measures the particle size distribution of optically dense slurries with undiluted, continuous, on-line sampling for real time process control. The probe includes a plurality of light sources, a detector system which includes one or more fixed grating linear detector array spectrometers and sample cells, a three position chopper, and an optical pathway for transmitting light from the light sources through the sample cells and then to the detector system or spectrometers. A computer or microprocessor receives detector signals, and performs a particle size distribution measurement. The sample cells are specially constructed to reduce optical depth in the slurry, which permits particle size distribution measurements without dilution of the slurry.

Optical depth is the dimensionless extinction parameter in the exponential transmission function of Beer's law, known in the art, and is defined as the product of an extinction per unit length in the slurry times a thickness of the slurry in an optical path through the sample cell. Optically dense slurry is hereby defined as a particulate poly-dispersion consisting of 1–30% solids by weight of sub-micron particles suspended in a liquid. CMP slurries are optically dense slurries that typically exhibit an optical depth of greater than 10, at 0.5 micron wavelength in a conventional sample cell having a one centimeter path length, yielding a transmission of less than 0.00005. As stated above, the reduction in optical depth derives from a substantial narrowing of the conventional flow path length in the sample cell to a length ranging from 50 to 250 (or more, depending upon system sensitivity) microns.

In one aspect, sample cells of the invention are formed of a chemically resistant housing that retains a first window and a second window in spaced relationship to provide a suitable optical depth. These windows are preferably made of a hard, chemically resistant, artificial crystal such as sapphire. The housing includes a tapered ramp that widens as it narrows from an inlet to the separation between the windows, and thins as it thickens from the separation to an outlet. The outlet preferably returns undiluted slurry to the day tank or main process slurry line after particle size distribution measurements have been obtained from the sample. The use of multiple sample cells yields measurements of greater accuracy by tuning the optical path length (i.e., window spacing) of each cell to a different wavelength regime. Specifically, greater accuracy measurements can be obtained by keeping the transmission, measured through the slurry, within the approximate range of 0.05–0.90.

In still another aspect, a light chopper is positioned between the light source and the sample cell. The chopper contains a plurality of holes for transmitting light to the sample cell and a plurality of mirrors or solid regions for blocking transmission of light to the sample cell. The mirrors allow measurement of the time and temperature drift of the sources, while the solid regions allow measurement of the time and temperature drift of the spectrometers and their detectors. These features provide autonomous operation in an industrial environment and eliminate the need for frequent measurement of reference spectra, which would require taking the probe off-line. The computer or microprocessor preferably uses a modified Twomey/Chahine-based nonlinear iterative conversion to calculate a particle size distribution measurement from the spectral transmission measurements. A plurality of fixed grating spectrometers each having a detector array can be used to assist in this calculation. An ultrasonic disrupter can also be used to disrupt soft slurry agglomerations just prior to their entry into the sample cell.

The probe of one aspect is operated continuously and in real time by diverting a portion of optically dense slurry from a main slurry line, introducing the slurry into a sample cell in undiluted form, narrowing the flow of the optically dense slurry within the sample cell to reduce optical depth in the slurry, transmitting light through the slurry, detecting light transmitted through the slurry in the sample cell with production of corresponding detector signals, and calculating a particle size distribution through use of the detector signals.

The invention also provides, in one aspect, a quality control process for detecting physical and/or chemical changes (e.g., changes in particle size distribution) of a CMP slurry. The process includes the steps of transmitting radiation, having one or more wavelengths, through a flow of the CMP slurry, determining transmission of the transmitted radiation at each of the wavelengths, and monitoring transmission, over time, to detect the changes in the CMP slurry. In one preferred aspect, the process detects changes in the particle size distribution of the CMP slurry.

The process of another aspect can include the step of determining a slope of transmission as a function of the wavelengths. The step of determining a change in the slope is preferably made "over time" such that a change in slope indicates a change in the particle size distribution. Further, the slope is preferably determined logarithmically. That is, the process preferably includes the step of determining a logarithmic slope of transmission as a function of the wavelengths.

In another aspect, the process includes the step of determining a change in the logarithmic slope over time. The change in logarithmic slope indicates change in the particle size distribution independent from a change in particle size concentration.

Preferably, the systems and methods of the invention detect and/or determine particle size distribution correspondingly centered about a value between about 0.03 and 1.0 micron, indicating a "good" CMP slurry in one aspect of the invention. Distributions centered about 0.1 to 1.0 micron, or higher (e.g., up to ten microns), are also possible in accord with the invention, correspondingly indicating "bad" CMP slurry, in one aspect of the invention.

In one aspect, the process of the invention determines a change in the particle size distribution, thereby indicating a quality control failure of the CMP slurry. Once detected, the change is preferably relayed to the user as a warning to inform the user of the failure. Other physical and/or chemical changes detected by the process can also relayed to the user as a warning, in accord with the invention.

In another aspect, the step of transmitting the radiation within the process includes transmitting the radiation through a sample cell selected on the basis of desired accuracy. The cell preferably defines a flow diameter such as 100 or 1900 microns.

Preferably, the process determines transmission with an accuracy of at least about 1%.

In one aspect, radiation wavelengths selected for transmission through the CMP slurry are isolated by a grating or other dispersive optical element (e.g., a prism). The wavelengths can alternatively be determined by using a laser with a known wavelength emission. In a preferred aspect, wavelength selection is made through use of one or more bandpass filters (and preferably two filters), such as within a filter wheel. A combination of the above spectral discriminators can also be used, as needed, in accord with the invention.

In yet another aspect, the process includes the further step of comparing the transmission to a reference transmission indicative of a preferred particle size distribution within a flow of the CMP slurry. Preferably, the process includes the further step of storing the reference transmission in memory so that a comparison can be made electronically and in real time.

Alternatively, the process can include the steps of (a) storing a plurality of reference transmissions, where each reference transmission corresponds to a particular CMP slurry flow and particle distribution, and (b) selecting one reference transmission and comparing the transmission to the selected reference transmission.

Particle sizes within the distribution are determined in one aspect of the invention through Mie scattering theory, known in the art of light scattering.

A process of the invention can further include comparing transmission information with an empirical curve of extinction efficiency versus particle size diameter to determine particle sizes within the distribution. Preferably, the particle size diameter includes a functional dependence of $\pi D/\lambda$, where D is the particle size diameter and lambda corresponds to wavelength associated with the transmission.

The invention also provides a system for evaluating CMP slurry quality in a process. In this aspect, a light source generates a beam of electromagnetic radiation for transmission through a flow of the slurry. A spectral discriminator isolates at least two wavelength bands of the radiation prior to transmission of the radiation through the flow. A detector detects radiation transmitted through the flow. A processor evaluates transmission of the wavelength bands through the flow to determine chemical and/or physical changes in the CMP slurry. By way of example, the processor of one aspect detects changes in the particle size distribution of the CMP slurry.

Preferably, the discriminator is a filter wheel. However, the discriminator can also be a grating or a prism. An order sorting filter is optionally included with these dispersive discriminators. Alternatively, a laser (e.g., a laser diode) can be used as the source and discriminator, since only a narrow band of wavelengths is emitted from the laser.

In one aspect, a computer with a processor serves as the processor of the system, to process signals and to make determinations and calculations. Those skilled in the art should appreciate that other processors, e.g., an ASIC, can alternatively be used.

In yet another aspect, a system of the invention includes memory, coupled to the processor, to store one or more reference transmissions. Each of the reference transmissions corresponds to a particular CMP slurry flow and particle distribution. The processor selects one reference transmission and compares the transmission through the flow to the selected reference transmission to detect changes in the particle size distribution. The memory can further store other reference data for comparison to other changes in physical and/or chemical characteristics of the CMP slurry, in accord with the invention.

In still another aspect, the memory of the invention can store data indicative of extinction efficiency as a function of particle size diameter. The processor then compares the transmission to the data to determine particle sizes within the distribution.

In another aspect, the processor calculates a logarithm of transmission at each wavelength band and to determine a change in slope of logarithmic transmission versus wavelength band. This enables the system to detect changes in the particle size distribution independently from changes in particle size concentration.

The invention is next described further in connection with preferred embodiments, and it will become apparent that various additions, subtractions, and modifications can be made by those skilled in the art without departing from the scope of the invention.

BRIEF DESCRIPTION OF THE DRAWINGS

A more complete understanding of the invention may be obtained by reference to the drawings, in which.

DETAILED DESCRIPTION OF THE DRAWINGS

Figure 1:
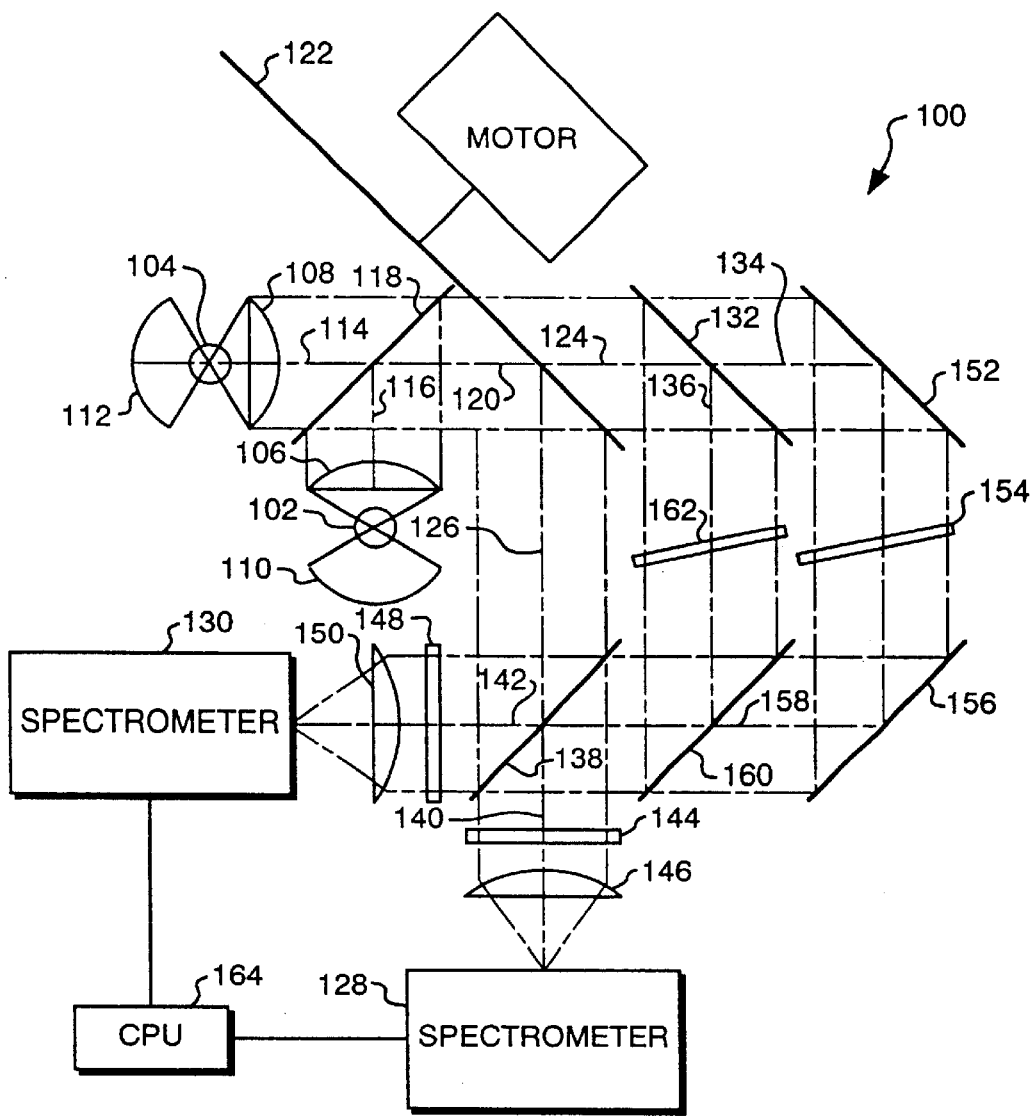
FIG. 1 schematically depicts a sample of a probe for use in measuring particle size distributions according to the invention.

FIG. 1 is an optical system schematic of a CMP slurry particle size distribution probe 100. A deuterium source 102 supplies ultraviolet radiation, while a quartz tungsten halogen source 104 supplies visible and infrared radiation. The light from each of sources 102 and 104 is collimated by a combination of a corresponding lens 106 and 108, and a corresponding a mirror 110 and 112, which provide respective collimated beams 114 and 116. A long pass filter 118 combines the two collimated beams 114 and 116 into a single collimated beam 120.

Figure 2:
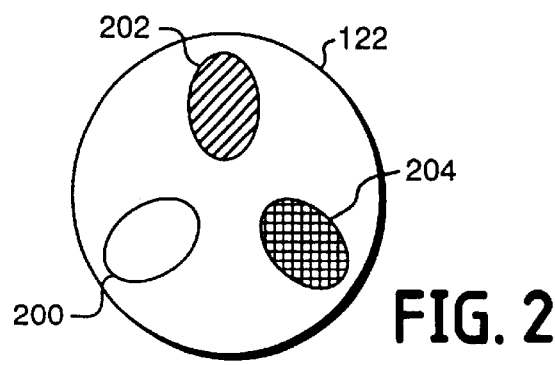
FIG. 2 depicts a light chopper blade for use in the probe of FIG. 1.

A motor-driven rotational chopper blade 122 intersects the combined collimated beam 120 and provides three different measurements in quick succession. As shown in FIG. 2, chopper blade 122 contains three ellipsoid features, namely, aperture 200, mirror 202, and solid, non-reflective disk 204. Aperture 200 permits transmission of light through chopper blade 122 for passage of collimated beam 120 onto pathway 124 (see FIG. 1). Mirror 202 allows measurement of source irradiance, which drifts with temperature and time, by reflecting light onto pathway 126. The solid disk 204 allows measurement of electronic offsets by preventing light from reaching the charge coupled device detector arrays within two miniature, fixed grating, linear detector array spectrometers 128 and 130. These electronic offsets are a substantial source of error for the detector arrays, if uncorrected, and the offsets drift with temperature and time.

Use of the mechanical chopper 122 permits real time calibration of probe 100 interspersed with actual measurement data, as facilitated by the respective optical pathways that are described below. Use of the mechanical chopper 122 also allows signal-to-noise enhancement associated with lock-in detection and signal processing techniques.

Light passing through hole 200 of chopper blade 122 travels on pathway 124 towards a long pass filter 132, which is used as a beam-splitter. For oxide CMP slurries, long wavelengths greater than about 0.55 microns pass through the long pass filter 132 onto pathway 134 while shorter wavelengths are reflected onto pathway 136. For metal CMP slurries, long pass filter 132 alternatively provides wavelength division at approximately 1.0 to 1.25 microns.

Light that is reflected from chopper blade 122 by mirror 202 travels along path 126 towards a 50/50 beam-splitter 138 for splitting of the light on pathway 126 into two beams 140 and 142 of equal intensity. Beam 140 travels through an order sorting or blocking filter 144 and gathering lens 146 towards the fixed grating spectrophotometer 128. Beam 142 travels through an order sorting or blocking filter 148 and gathering lens 150 towards the fixed grating spectrophotometer 130. Order sorting filters 144 and 148 prohibit higher order diffraction of the fundamental wavelength by gratings within the spectrometers 128, 130, respectively. It is anticipated that the wavelength coverage of the two spectrometers 128 and 130 will be approximately be 0.20 to 0.50 microns and 0.50 to 1.0 microns respectively for oxide CMP slurries, and 0.5 to 1.0 microns and 1.25 to 2.5 microns respectively for metal CMP slurries. Spectrometers operating at wavelengths shorter than 1.0 micron can utilize Si detector arrays, and those operating at longer wavelengths can utilize InGaAs detector arrays.

Light passing through long pass filter 132 onto pathway 134 is directed towards a first mirror 152 for reflection through a first sample cell 154. Light that has been transmitted through first sample cell 154 is reflected by a second mirror 156 along pathway 158 through long pass filter 160. Long pass filter 160 is preferably identical to long pass filter 132, and both filters may be changed to provide appropriate instrument sensitivity in the intended environment of use. Light on pathway 158 passes through long pass filter 160, and is eventually split 50/50 by beam splitter 138 for delivery to spectrophotometers 128 and 130.

Light reflected by long pass filter 132 onto pathway 136 travels through a second sample cell 162. Light that has been transmitted through the second sample cell 162 is reflected by long pass filter 160 towards beam-splitter 138 for 50/50 delivery of light to spectrophotometers 128 and 130. The use of multiple sample cells yields measurements of greater accuracy by tuning the optical path length (window spacing) of each cell to a different wavelength regime. Tuning is accomplished by maintaining transmission through the cells in a range between about 0.10 to 0.90.

Spectrometers 128 and 130 are collectively referred to herein as a detector or detector group. Each spectrometer preferably includes an internal fixed grating to enhance speed of measurement and reliability, i.e.; the preferred spectrometers are not scanning spectrometers having a movable grating. The internal fixed grating (not shown) is configured to place dispersed light having selected wavelengths on an internal array of conventional detector elements concealed within each spectrometer. Thus, each spectrometer is operable to detect a range of wavelengths. A computer 164 receives signals from the detector group including spectrophotometers 128 and 130, and uses these signals to either (a) calculate a particle size distribution corresponding to the CMP slurry being measured and/or (b) detect changes in the particle size distribution for quality control purposes.

In embodiments where the slurry is not optically dense, sample cells 154 and 162 may be removed to provide an open pathway adapted to receive a pharmaceutical mist, such as a mist from a medical nebulizer for delivery of medication to asthmatics. The sample cells may also be replaced by an open tube or chamber. In this manner, probe 100 is used to measure (a) the particle size distribution of aerosol mists and/or (b) changes in the particle size distribution for quality control purposes.

Figure 3:
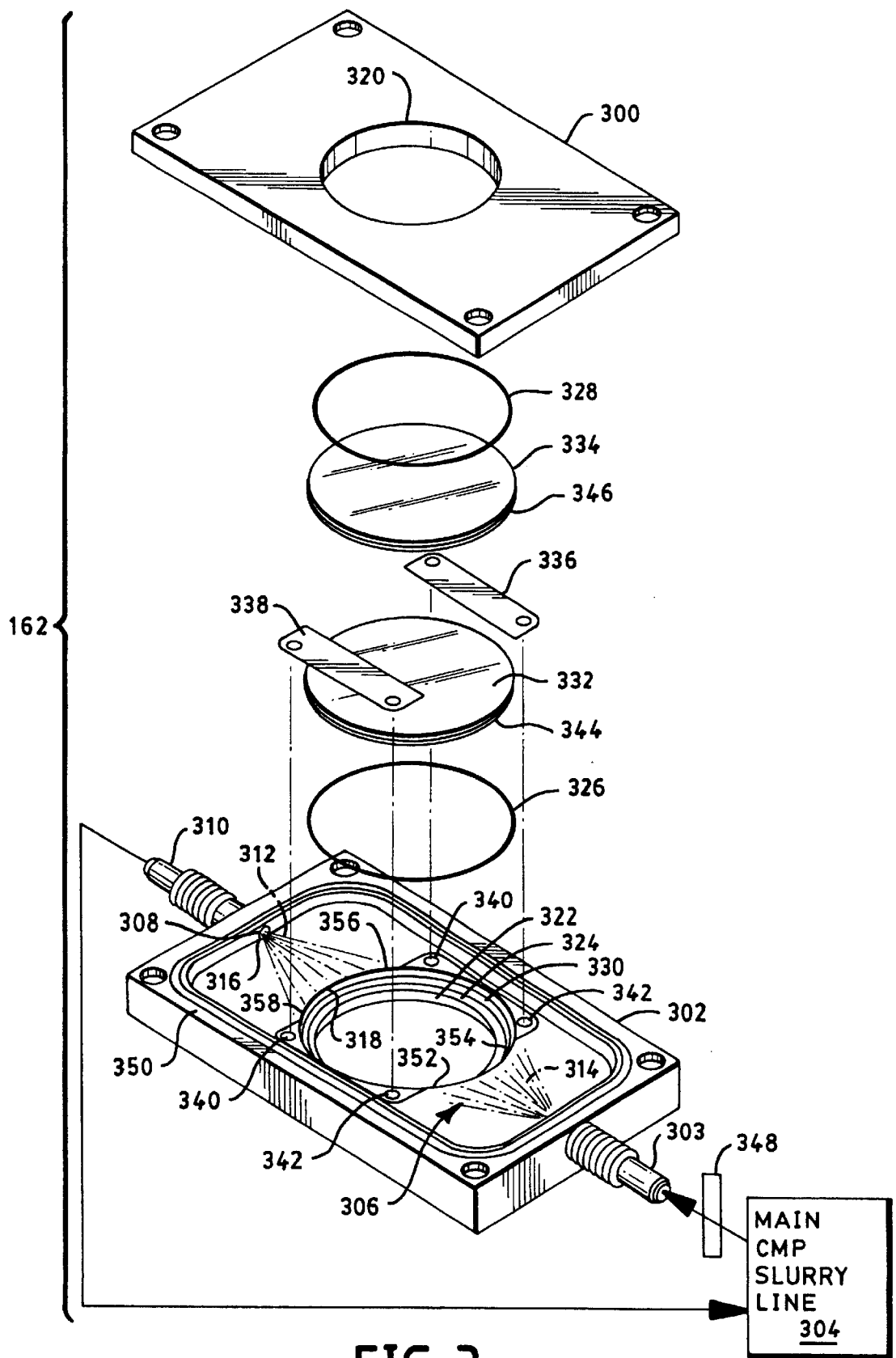
FIG. 3 depicts, in an exploded view, a first specially constructed sample cell for use in the probe of FIG. 1.

FIG. 3 gives a detailed assembly view of a preferred CMP slurry sample cell 162 (see FIG. 1), which is intended for use with optically dense slurries. Both cells 154 and 162 share the same basic features, but the depth of the cells may be selectively adjusted to accommodate increasing transmissivity of longer wavelength radiation in cell 154 (see FIG. 1).

A housing is formed of top plate 300 and bottom plate 302, which are each machined from a solid block of chemically resistant material such as Kel-F, polyvinyldifluoride ("PVDF") or polyvinyldichloride ("PVDC"). Sample cell inlet line 303 is connected with an inlet port (not depicted) through which undiluted CMP slurry from main CMP slurry line 304 enters the interior space 306 of sample cell 162. Outlet port 308 drains the slurry from space 306 into outlet line 310. Each of top plate 300 and bottom plate 302 are provided with an opposed pair of triangular tapered ramps, e.g., ramps 312 and 314. These ramps are thickest at their respective tips proximate the corresponding port, e.g., tip 316 proximate outlet port 308, and which widen and narrow towards a base remote from the port, e.g., base 318.

Each of top and bottom plates 300 and 302 are respectively provided with centrally located circular apertures 320 and 322. The interior portions of plates 300 and 302 contain a groove 324, for receipt of corresponding elastomeric O-rings 326 and 328. A bevel 330 receives sapphire windows 332 and 334. A pair of opposed spacers 336 and 338 are retained against flow by corresponding retaining pins, e.g., retaining pins 340 and 342, and fit between sapphire windows 332 and 334.

Sapphire windows 332 and 334 and opposed spacers 336 and 338 define the optical viewing area available to path 136 (see FIG. 1). The optical viewing area preferably ranges between 50 and 250 microns in thickness between windows 332 and 334 for use with optically dense slurries. In one embodiment, the optical viewing area can be upwards of 1900 microns. Slurry fills the space between the two sapphire windows 332,334, and the transmission path length through sample cell 162 equals the thickness of spacers 336 and 338. The tapered ramps 312 and 314 are carefully machined into the respective plates 300 and 302 to provide a smooth transition between the input/output lines 303 and 310, and the optical viewing area. This smooth transition prevents slurry agglomeration. Also the inside edges of sapphire windows 332,334 have been beveled, as at bevels 344 and 346 to prevent slurry accumulation and agglomeration.

An ultrasonic generator or disrupter 348 is optionally coupled with the sample cell input line 303 for disruption of soft slurry agglomerates. CMP slurry can contain both hard and soft agglomerates, and the soft agglomerates are believed not to scratch semiconductor wafers. Ultrasonic disrupter 348 breaks up the soft agglomerates before slurry enters the sample cell.

Slurry enters the space defined by spacers 336 and 338 and between windows 332 and 334. Cell 162 is referred to herein as a non-volumetric sample cell for the reason that some leakage may escape into the cavity 350 surrounding the opening 322, e.g., through non-sealed openings at 352, 354, 356, and 358. This leakage, as well as the flow between windows 332 and 334, is collected by ramp 312 and cell output line 310. Slurry between windows 332 and 334 is exposed to light or electromagnetic radiation from pathways 134 or 136 for particle sensing and analysis by CPU 164 (see FIG. 1).

Figure 4:
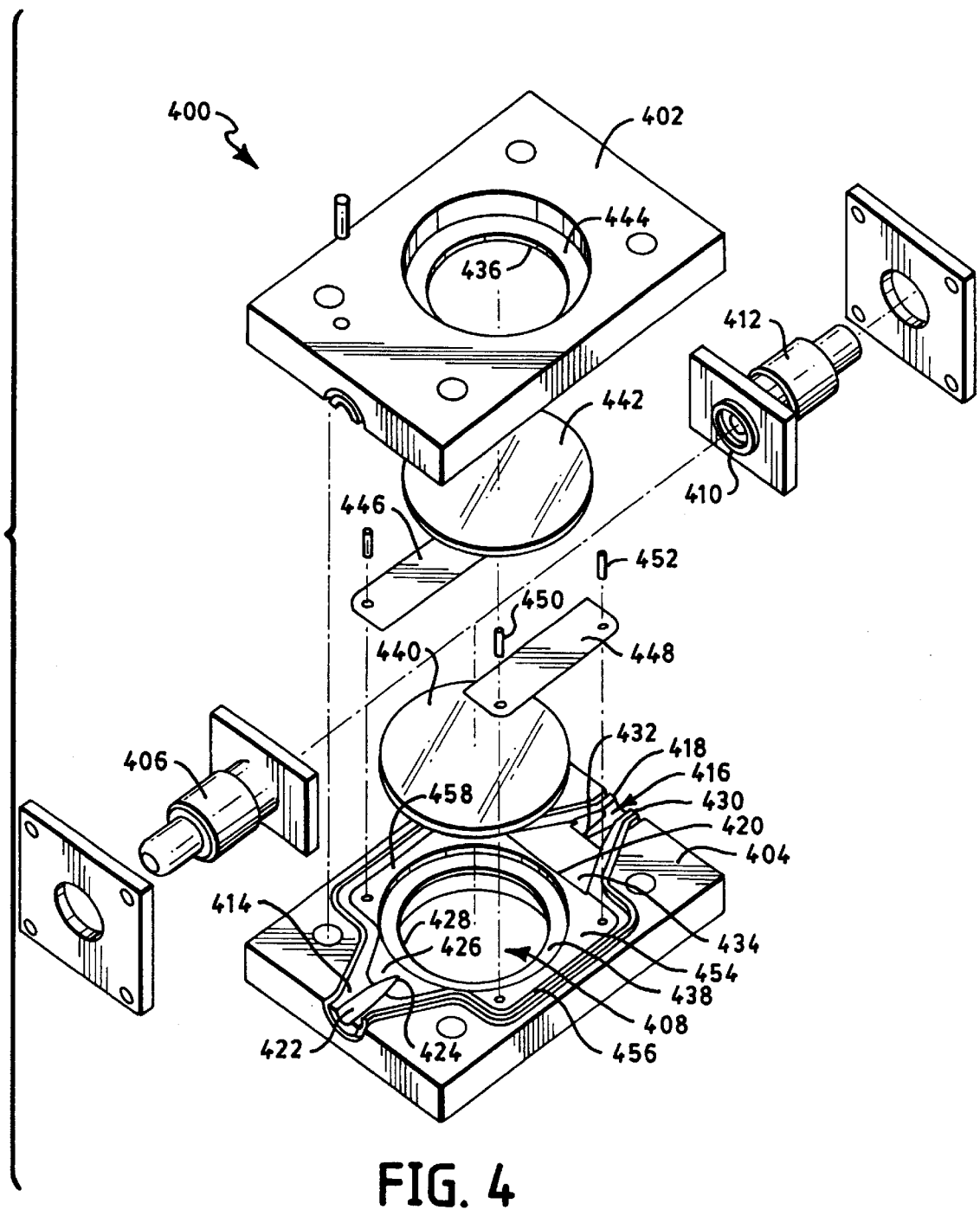
FIG. 4 depicts, in an exploded view, a second specially constructed sample cell for use in the probe of FIG. 1.

FIG. 4 depicts a second and most preferred volumetric sample cell 400 for use as Aid an alternative to, or in combination with, sample cells 162 or 154 of FIGS. 1 and 3. A housing is formed of top plate 402 and bottom plate 404, which are each machined from a solid, slightly deformable block of chemically resistant material such as TFE Teflon. Sample cell inlet line 406 is connected with an inlet port (not depicted) through which undiluted CMP slurry from the main CMP slurry line enters the interior space 408 of sample cell 400. Outlet port 410 drains the slurry from space 408 into outlet line 412. Each of top plate 402 and bottom plate 404 are provided with an opposed pair of triangular tapered ramps, e.g., ramps 414 and 416. These ramps are thickest at their respective tips proximate the corresponding port, e.g., tip 418 proximate outlet port 416, and which widen and narrow towards a base remote from the port, e.g., base 420. Ramp 414 contains a conical opening having a maximum volume proximate cell inlet line 406. This volume decreases towards ramp 416 with decreasing volume in the conical opening 422 being equally compensated by increased volume in the portion of ramp 414 surrounding conical opening 422. Conical opening 422 terminates at tip 424 proximate a wedge 426 of increasing narrow width and steepness leading to an interior opening 428. Ramp 416 has a similar conical opening 430 with tip 432 pointing towards ramp 414 and terminating prior to wedge 434.

Each of top and bottom plates 402 and 404 are respectively provided with centrally located circular apertures 428 and 436, which are slightly offset along the fluid flow axis. The interior portions of plates 402 and 404 each contain a first step surrounding the corresponding opening, e.g., first step 438 surrounding opening 428, for receipt of a corresponding sapphire window. For example, a flat sapphire window 440 is received in sealing engagement against step 438. Flat sapphire window 442 identical to window 440 is similarly received in sealing engagement against step 444. A pair of opposed spacers 446 and 448 are retained against flow by corresponding retaining pins, e.g., retaining pins 450 and 452, and fit between the sapphire windows 440 and 442. Each spacer is retained within the confines of a correspondingly sized recess, e.g., as spacer 448 is retained within recess 454. A deformable elastomeric wall 456 sealingly engages top plate 402 and bottom plate 404 to prevent leakage from sample cell 400. Wedges 426 and 434 extend wide enough to meet the spacers 448 and 446. Spacers 446, 448 each sealingly engage both windows 440 and 442. Thus, there is no slurry leakage from the space between windows 440 and 442, i.e., cell 400 is a volumetric cell because it does not leak into space 458 circumscribing windows 440 and 442. The optical viewing area between windows 440 and 442 preferably ranges between 50 and 250 microns (and up to about 2000 microns in certain embodiments) in thickness for use with optically dense slurries.

Sample cell 400 operates in a similar manner with respect to cell 162, shown in FIG. 3, though there are volumetric flow differences between the two cells 162,400 with respect to leakage from the space between the windows. The sapphire windows 440 and 442 together with opposed spacers 446 and 448 define the optical viewing area available to path 134 or 136 (see FIG. 1). The slurry fills the space between the two sapphire windows, and the transmission path length through sample cell 400 equals the thickness of spacers 446 and 448. The tapered ramps 414 and 416 are carefully machined into the corresponding plates 402 and 404 to provide a smooth transition between the input/output lines 406 and 412 relative to the optical viewing area between windows 440 and 442. This smooth transition prevents slurry agglomeration.

The various optical pathways depicted in FIG. 1 comprise a distance along which light may travel. In alternative embodiments, the pathways 114, 116, 120, 124, 126, 134, 40, 142, and 158 may be constructed of optical fibers. In this alternative embodiment, mirrors 152 and 156 are not required. Long pass filters 118, 132, and 160 may be replaced by 1:2 fiber optic couplers. A 1:2 fiber optic coupler may also replace the 50:50 beam splitter 138.

Measurement of light scattering as a function of angle is also a sensitive measurement technique for CMP slurry particle size distribution. A major disadvantage of this approach is that significant multiple scattering errors appear when the optical depth exceeds 0.1–0.2, where the optical depth is the product of the extinction per unit length times the sample cell thickness. This measurement technique relies upon an unambiguous definition of the scattering angle for each photon. For a doubly scattered photon, the scattering angle for each scattering event is undefined. This limitation necessitates a batch sampling mode of operation, with large amounts of dilution.

By comparison, the spectral transmission measurement technique can operate at optical depths as large as approximately 3.0, allowing one to sample undiluted slurry in a continuous, real time mode, with realistic sample cell dimensions. The spectral transmission measurement technique does not suffer from multiple scattering errors until the diffuse radiation field intercepted by the sensor's narrow field of view (typically about 1°), becomes a significant percentage of that remaining in the direct beam.

Mie scattering gives a complete theoretical description of optical extinction by homogenous spheres. Although particles in all of the CMP slurries are chemically homogeneous, i.e., they are composed of a single known compound, most particles are not spherical. Even so, Mie theory has demonstrated success by modeling the optical extinction of naturally occurring, non-spherical particles in terms of optically equivalent spheres. Furthermore, extinction is the sum of scattering over all angles plus absorption, and is not as sensitive to particle shape as is the scattering phase function (the angular scattering pattern).

The slurry particle size distribution (PSD) is retrieved from the spectral transmission measurements through utilization of a modified Twomey/Chahine nonlinear inversion algorithm. Equation (1) expresses the measured transmission (T) as a function of wavelength ($\lambda$) in terms of the transmission of sample cell windows ($T_W$), the transmission of the liquid portion of the slurry ($T_L$), and the transmission of the slurry particles ($T_P$).

$$T(\lambda)=T_W(\lambda)T^L(\lambda)T_P(\lambda) \tag{1}$$

By first measuring the transmission of the sample cell filled only with the liquid portion of the slurry, then dividing that into the transmission expressed in Equation (1), one can isolate $T_P(\lambda)$, which is the quantity of interest. Beer's Law is then solved for the particle volume extinction coefficient ($\beta E(\lambda)$), as shown in Equation (2), where L is the transmission path length or sample cell width. Equation (3) represents the formula for calculating the particle volume extinction coefficient in terms of the particle radius (r), the Mie extinction efficiency ($Q_E$), and the PSD (N(r)), where m is the particle's complex refractive index.

$$\beta_E(\lambda)=-\ln(T_P(\lambda))/L \tag{2}$$

$$\beta_E(\lambda)=\int \pi r^2 Q_E(2\pi r/\lambda)N(r)dr \tag{3}$$

Equation (3) is inverted to solve for the particle size distribution. One class of inversion algorithms is the linear inversion, which provides a less preferred model for reasons that are explained below. The less preferred inversion method transforms the measurement equation into a linear system of equations by replacing the integral with a summation and by representing the collection of equations in the matrix form given by Equation (4). In this latter equation, elements of matrix Q consist of $\pi r^2 Q_E$. The Q matrix has m rows, one for each wavelength, and n columns, one for each radius; m must be greater than or equal to n. The N matrix is n by 1, and the elements consist of the particle size distribution. The $\beta$ matrix is m by 1, and the elements consist of the measured spectral volume extinction coefficients.

$$Q_R N_R = \beta_\lambda \tag{4}$$

Equation (4) can be formally inverted to solve for the particle size distribution, utilizing conventional inversion algorithms which constrain the solution to various conditions, such as smoothing (minimize the first or second derivative), or minimize the departure from a first guess, according to Twomey, *Comparison of constrained linear inversion and an iterative nonlinear algorithm applied to the*

*indirect estimation of particle size distributions*, J. comp. Phys., Vol. 18, No. 2, pp. 188–200 (1975), which is hereby incorporated by reference to the same extent as though fully disclosed herein.

Constraints are required in all inversion algorithms because the existence of measurement error and quadrature error (replacing the integral with a sum) result in the fact that a family of partide size distributions will satisfy the measurement equation. For any inversion method, the uncertainty in the retrieved solution can be reduced by: (a) choosing a more sensitive measurement technique, (b) reducing the measurement error, (c) increasing the number of measurements, which reduces the effects of quadrature error.

Linear inversion techniques are computationally efficient, but they are a poor choice for the CMP slurry problem because the most popular constraint, i.e., that of smoothing, is a poor choice for slurry particle size distributions. These distributions are not necessarily smooth or continuous. Additionally, linear inversion algorithms can be unstable to an extent that produces physically unrealistic answers.

The CMP slurry measurement problem consists of detecting departures from the normal or specified particle size distribution, which makes a non-linear, iterative, inversion algorithm a natural choice and a more preferred model for use in practicing the invention. With the iterative approach, one can start with the normal particle size distribution as a first guess. The iterative calculations converge toward a final solution in an orderly fashion, where convergence is based upon a difference between the measured spectral extinction and that calculated from the last guess particle size distribution. Alternatively, one can start with a delta function as a first guess. Iteration is halted when this difference becomes less than some predetermined error bound. This preferred method of inverting equation (4) is based on previous work in the field of atmospheric remote sensing by Cerni, *Aircraft-based remote sensing or tropospheric profiles for meoscale studies*, Advances in Remote Sensing Retrievals, pp. 339–347 A. Deepak Publ., Hampton, Va. (1985); and Chahine, *Inverse problems in radiative transfer: Determination of atmospheric parameters*, J. Atmos. Sci., Vol. 27, pp 960–967 (1970) and Twomey (1975, referenced earlier), which are incorporated by reference herein to the same extent as though fully disclosed herein.

The algorithm given in Equations (5) and (6) is a preferred means of inverting the spectral transmission data to retrieve the particle size distribution. The superscripts I and I–1 refer to successive numbers of iterations. The subscripts P refer to different wavelengths, and indicate that all the measurements are utilized in adjusting the partide size distribution at a single r value. Additionally, one can improve the accuracy of the retrieval by adding conservation of mass (slurry percent solids by weight), and summing Equation (5) over all wavelengths.

$$N_P^{(I)}(r) = [1 + (r_P^{(I-1)} - 1)\pi r^2 Q_E(2\pi r/\lambda, m)] N_P^{(I-1)}(r) \quad (5)$$

$$r_P^{(I-1)} = \beta_E(\lambda) / [\int \pi r^2 Q_E(2\pi r/\lambda, m) N_P^{(I-1)}(r) dr] \quad (6)$$

EXAMPLE 1 VERIFICATION OF THE MODEL WITH EXPERIMENTAL RESULTS

Mie theory optical model results were verified with the use of an Acton SP-305 spectrometer system retrofitted with a sample cell according to FIG. 3. The sample cell was constructed to provide sapphire windows having a 40 mm diameter with the windows being held approximately 100 microns apart in a PVDF chemically resistant block. The detector module utilized one Si and one InGaAs photodiode to cover the broad 0.20–2.5 micron spectral range.

Figure 5:
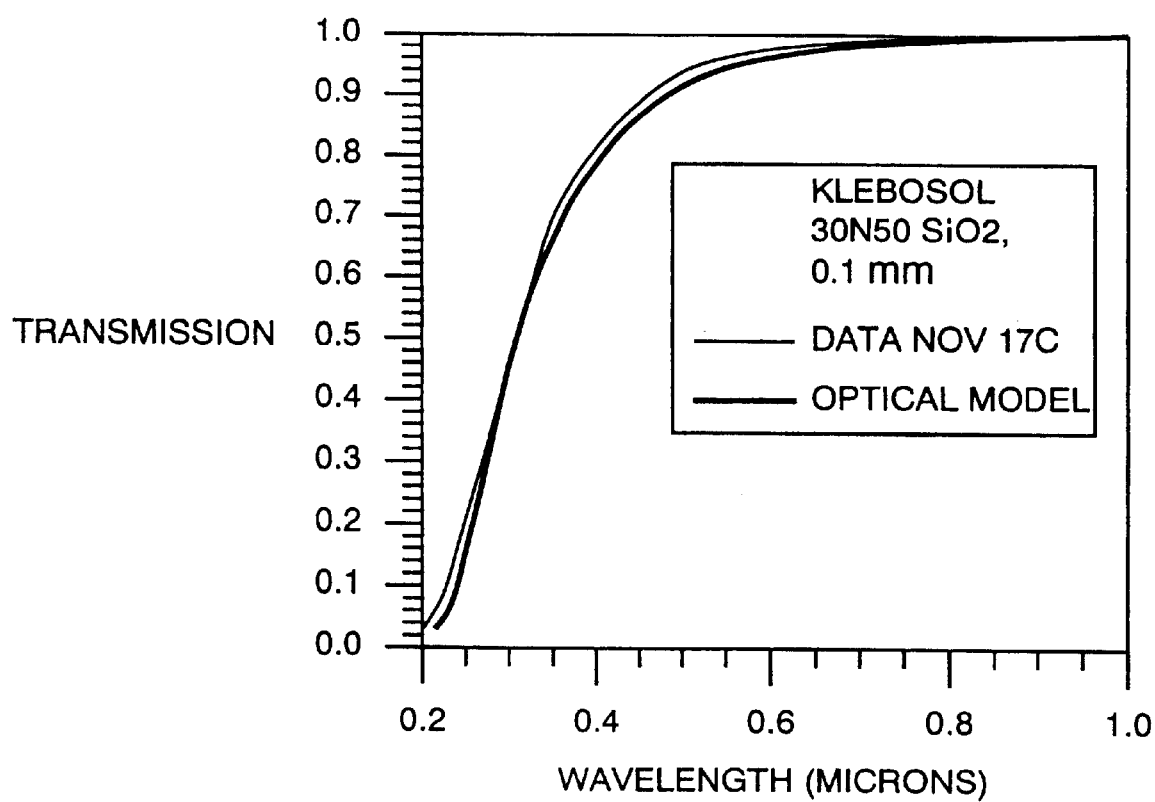
FIG. 5 depicts a comparison between (a) calculation data from an optical model of the invention and (b) spectral transmission data obtained from a manufacturer's CMP slurry.

FIG. 5 shows a comparison between optical model predictions and experimental data for Solution Technology Klebosol 30N50 oxide slurry, which consists of $SiO_2$ particles immersed in a weak $NH_4OH$ solution with a pH of 10.9. The product as tested contained 30% solids by weight, which is the basic product produced by Solution Technology. The product it is typically diluted to 18% solids by weight just prior to use in CMP wafer planarization. Thus, the tested product was even more optically dense than an actual CMP slurry using the product. As an input, the optical model utilized a particle size distribution provided by Solution Technology, shown in FIG. 6, which the manufacturer purports to have been measured with an electron microscope. The comparison shown in FIG. 5 demonstrates a remarkably good agreement between measured transmission data and optical model predictions.

Possible reasons for the observed small differences between the two curves (theoretical and actual results) of FIG. 5 include: (1) departure of the optical behavior of this unusually dense particulate suspension from that predicted by Mie theory, (2) departures of the sample particle size distribution from the typical particle size distribution provided by the slurry manufacturer, (3) errors in the particle size distribution measurements provided by the slurry manufacturer, due to the poor sample statistics provided by analysis of electron microscope imagery, (4) unexpected slurry liquid absorption bands, and (5) errors in the experimental spectral transmission measurement technique. The combined effects of these error sources are minor in this example. Klebosol 30N50 is described by the manufacturer as consisting of individual spheres, which are grown from seed in a saturated $SiO_2$ solution. As such, one would expect accurate predictions from Mie theory.

The experimental data shown in FIG. 5 was truncated at a transmission value of 0.030, below which the measured data indicated a leveling off and then an increase in transmission as wavelength decreased and optical depth increased. Such a result is unphysical, and indicates that the multiply scattered radiation, which is scattered in a near forward direction, has become comparable to or greater than the transmitted radiation. This result is expected to occur at some point with increasing optical depth and with a finite instrument field of view. The detector system utilized the SP-305 spectrometer, which is designed to have a nominal 1° field of view; and this scattering effect was predicted to be observed at a transmission value of approximately 0.050, i.e., an optical depth of 3.

EXAMPLE 2 VERIFICATION OF THE MODEL WITH EXPERIMENTAL RESULTS

Figure 7:
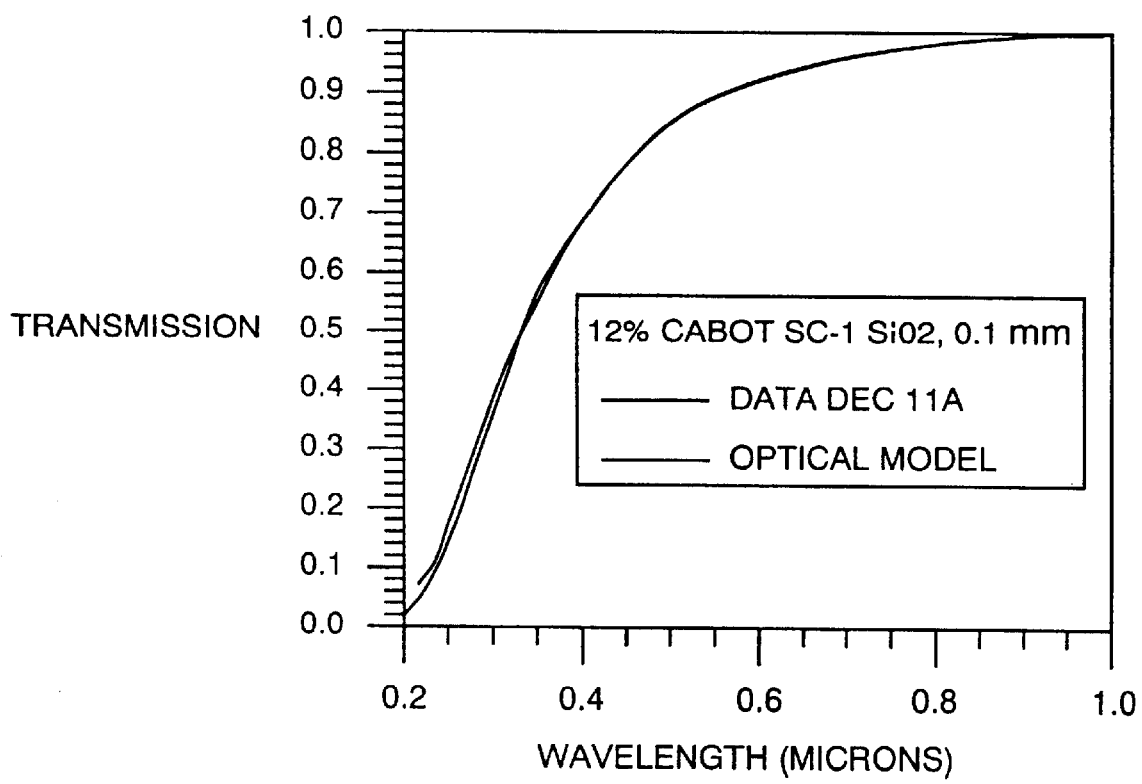
FIG. 7 depicts a comparison between (a) calculation data from an optical model of the invention and (b) spectral transmission data obtained from a manufacturer's CMP slurry.
Figure 8:
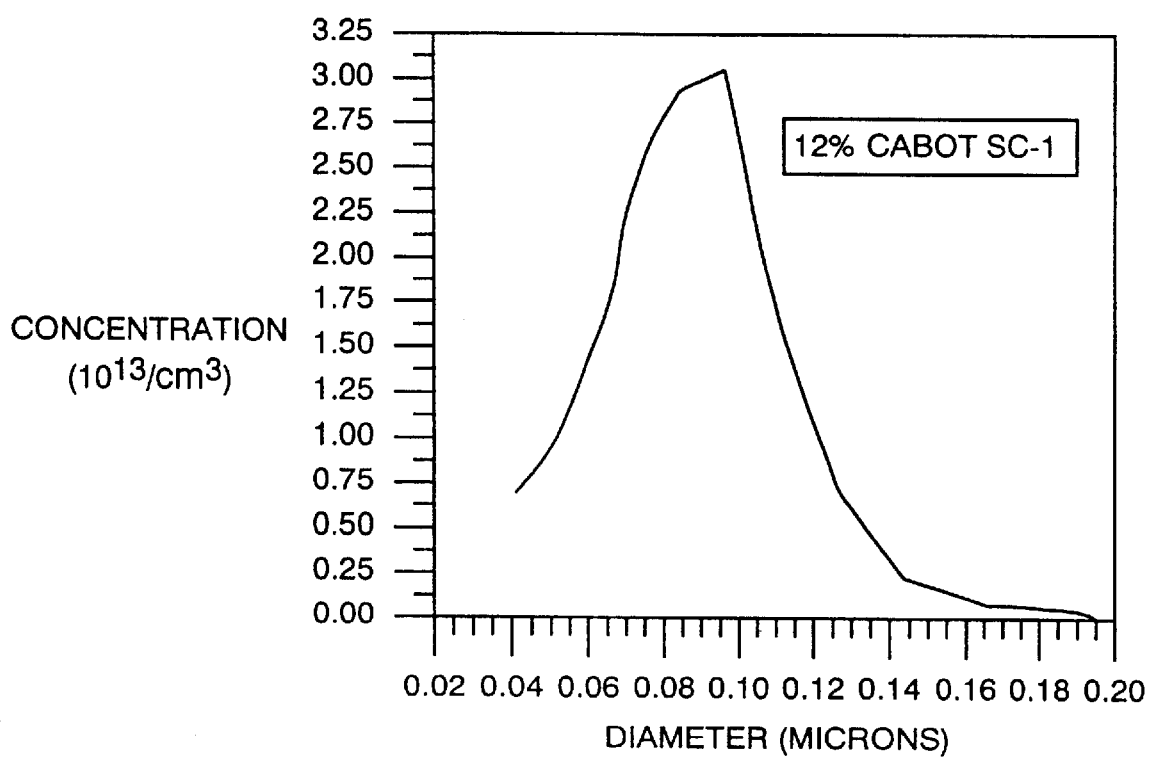
FIG. 8 depicts reported data for a particle size distribution corresponding to the spectral transmission data of FIG. 7.

FIG. 7 shows optical model predictions and experimental data for Cabot SC-1 oxide slurry, which consists of $SiO_2$ partides immersed a pH of 10.3. This sample was diluted to 12% solids by weight, which is the concentration at which it is used for CMP wafer planarization. The particle size distribution used as input to the optical model is plotted in FIG. 8, and represents a modified version of the Cabot SC-1 PSD measured by Bare et al., *Monitoring slurry stability to reduce process variability*, Micro. Vol. 15, No. 8, pp. 53–63 (1997) (the BH97 particle size distribution distribution probe. A modification to the BH97 particle size distribution consisted of multiplying each particle size distribution size bin by 0.56. The 0.56 factor was chosen to obtain good fit to the measured transmission data.

Figure 9:
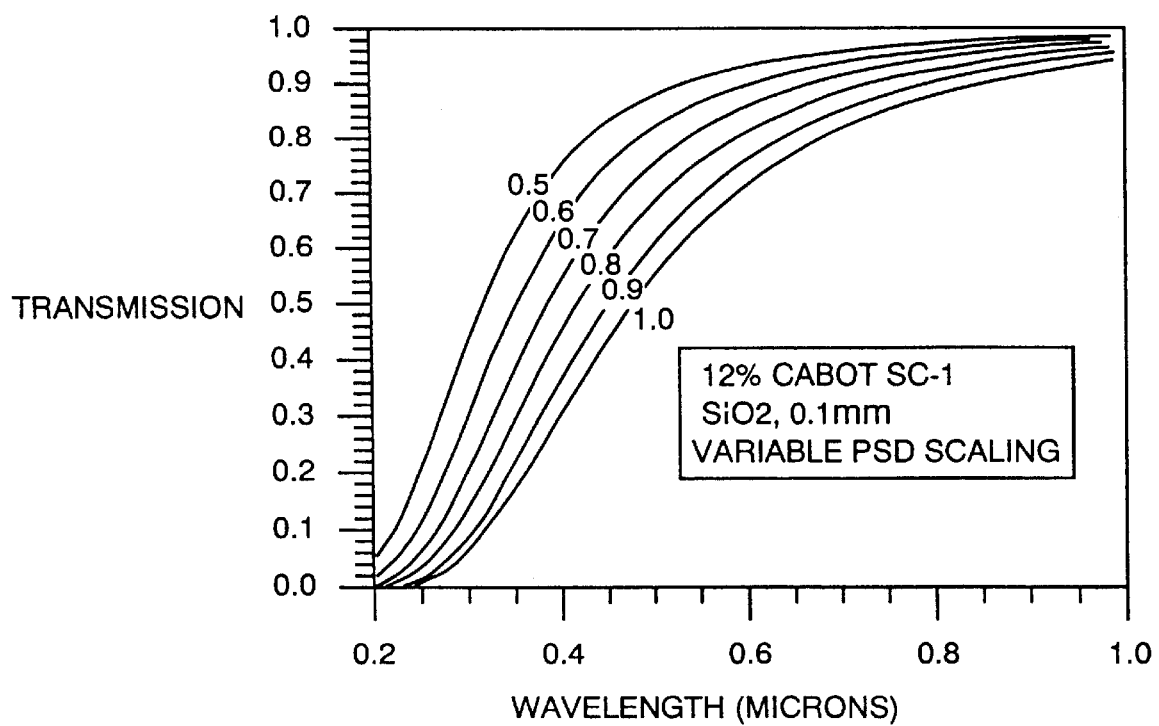
FIG. 9 depicts the calculated spectral transmission data effects of varying a distribution size bin factor to adjust the particle size distribution data shown in FIG. 10.
Figure 10:
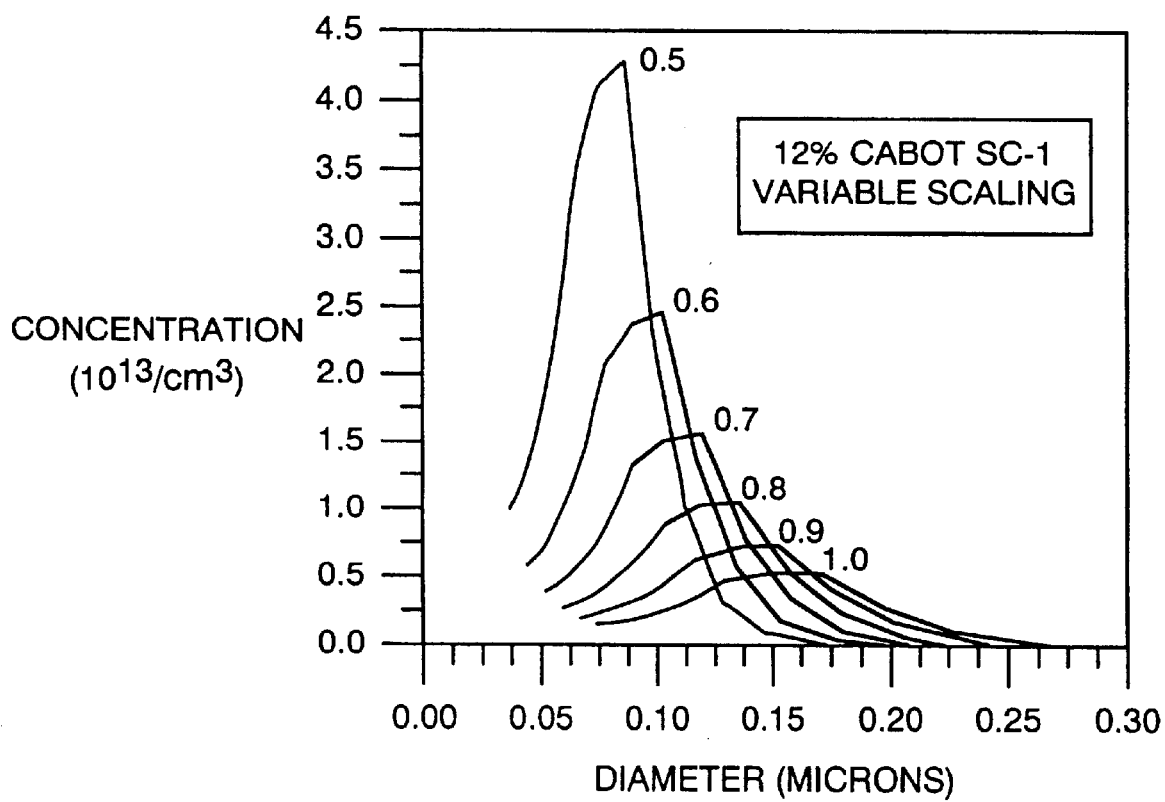
FIG. 10 depicts the calculated concentration data effects of varying a distribution size bin.

FIGS. 9 and 10 show how changes in this distribution size bin factor affect the transmission spectrum, and serve as another indication of the sensitivity of the spectral transmission measurement technique. Cabot SC-1 is a fumed silica product produced by combining reactant gases in a flame, and is known to consist of chains of tiny spheres fused together. Hence, the diameter of such a particle chain is not well defined. The extinction cannot be accurately modeled by Mie theory, and one should expect differences in the particle size distribution obtained by different measurement techniques. Given this uncertainty, a factor of 0.56 is reasonable.

In FIG. 9, the measured spectrum was truncated at a transmission value of 0.079, due to apparent errors introduced by multiple scattering. This higher value of transmission cut-off for SC-1 versus 30N50 (0.079 versus 0.030, above), is consistent with the larger particles present in the former slurry, which is known to produce more forward scattering. It is also consistent with more forward scattering produced by nonspherical versus spherical particles.

Figure 11:
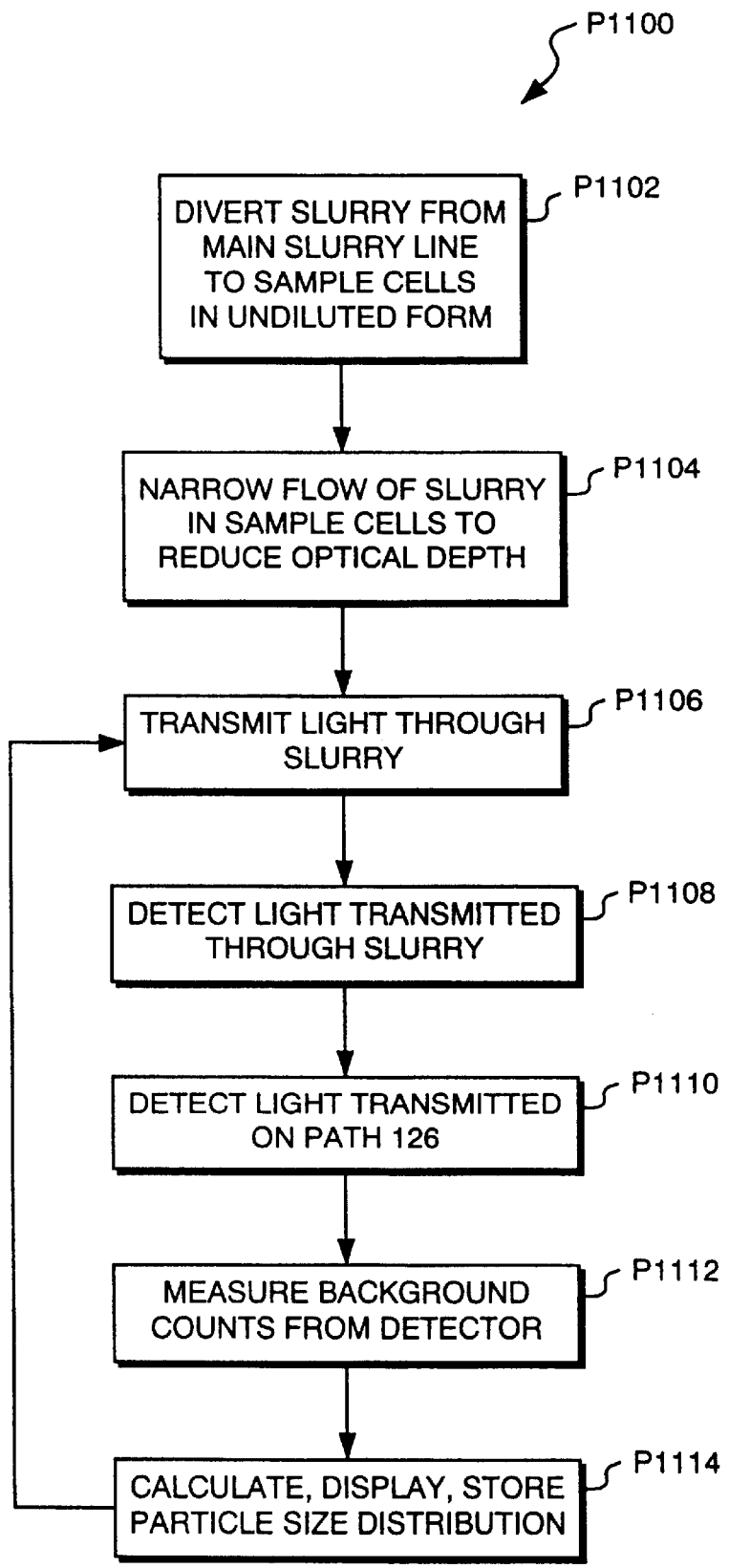
FIG. 11 depicts a schematic process diagram for use in operating the probe shown in FIG. 11.

FIG. 11 depicts a schematic process diagram of process P1100 for use in operating the probe shown in FIG. 1. In step P1102, optically dense CMP slurry is diverted from the main slurry line to the sample cells 154 and 162. In step P1104, the flow of slurry is narrowed through the sample cells to provide an optical depth that permits meaningful spectral transmission data. Light is transmitted through the narrowed slurry along pathways 134 and 136 in step P1106. Pathways 140 and 142 deliver this light to the spectrophotometers 128 and 130 in step P1108. The spectrophotometers produce signals representative of the detected light and particles in the cells 154 and 162. These signals are transmitted to CPU 164 for processing according to the modified Twomey/Chahine technique according to equations 1–6.

At the conclusion of step P1108, step P1110 includes the detection of light transmitted along pathway 126 to spectrophotometers 128 and 130 due to the rotation of chopper blade 122 and the reflective action of mirror 202. The detector counts are transmitted to CPU 164 for registration of source lighting conditions without particle scattering from sample cells 154 and 162.

In step P1112, the detector background count is measured with chopper blade 122 positioned to place solid disk 204 in path 120 for blocking the transmission of light along either path 126 or 134. Spectrophotometers 128 and 130 again produce signals corresponding to detected light, and these signals are transmitted to CPU 164, which interprets the signals as background count information that can be subtracted from total counts received from light traveling along pathways 126 or 134.

In step P1114, CPU 164 uses stored detector signals from steps P1108, P1110, and P1112 to calculate, display and store a particle size distribution, as discussed above. Steps P1106–1114 are continuously repeated to perform real time measurements of the particle size distribution in the CMP slurry.

Figure 12:
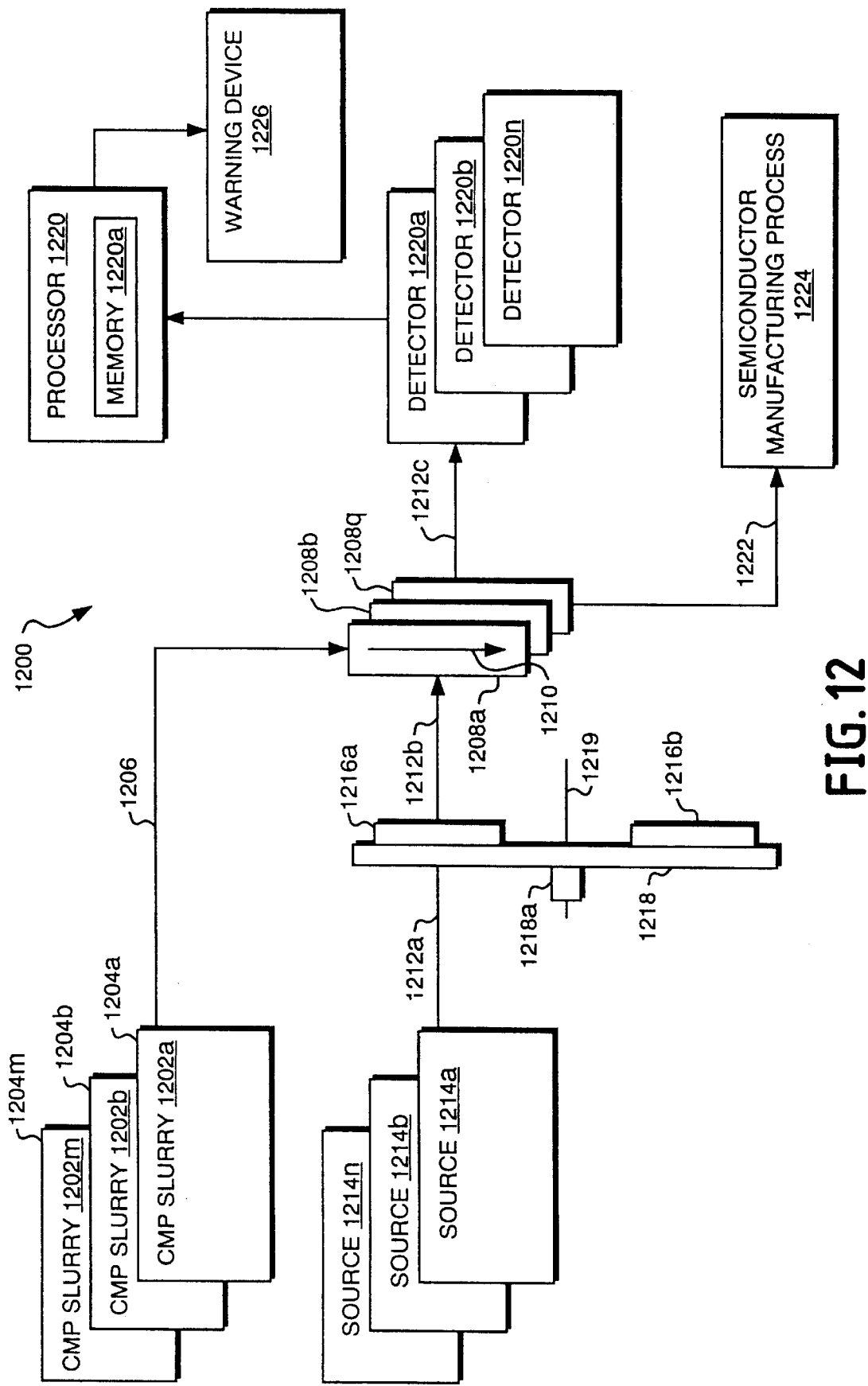
FIG. 12 illustrates a CMP slurry quality control system constructed according to the invention.

FIG. 12 shows one CMP slurry quality control system 1200 constructed according to the invention. CMP slurry 1202 from CMP slurry supply 1204 is transmitted through supply line 1206 to a sample cell 1208, e.g., sample cells 154, 162 of FIGS. 1 and 3. Sample cell 1208 provides for efficient and uniform CMP slurry flow 1210 through cell 1208 so that radiation 1212 may be transmitted therethrough, as discussed in FIG. 1 above in connection with beams 134, 136.

Source 1214 generates radiation 1212. By way of example, source 1214 can be a quartz tungsten halogen source, generating infrared and/or visible radiation 1212, or a deuterium source, generating ultraviolet radiation. Preferably, source 1214 is "broadband" so as to provide multiple wavelength bands which generate radiation 1212. However, multiple sources 1214a, 1214b . . . 1214n can be used, selectively, to generate desired radiation wavelengths 1212a, as required. For example, to generate ultraviolet light, source 1214b can represent a deuterium source; while to generate infrared or visible light wavelengths, source 1214a can represent a tungsten lamp. To switch between sources 1214, an arrangement such as shown in FIG. 1 can be used, or alternative techniques can be used to accomplish the same function, such as through mechanical actuation.

In the preferred embodiment, filters 1216 spectrally discriminate source radiation wavelengths 1212a emitted from source 1214 such that only selected wavelengths 1214b pass through filters 1216. Multiple filters 1216a, 1216b can be used to alternatively pass and select different wavebands to illuminate sample 1208. By way of example, filters 1216 are shown arranged on filter wheel 1218 which is rotated about axis 1219 by motor controller 1218a, selectively, to alternatively position filters 1216a, 1216b in the path of radiation 1212a. Filter wheel 1218, controller 1218a, and filters 1216 are known those skilled in the art of optics. In this manner, radiation 1212b of desired waveband can be selected by a user of system 1200. Filters 1216 are moved to block radiation 1212a as needed to select the appropriate wavelength band as emitted from source(s) 1214.

Although two filters 1216 are shown, those skilled in the art should appreciate that one or more filters can be used in system 1200 to achieve the objectives herein.

Radiation 1212c transmitted through sample cell 1208 corresponds to radiation also transmitted through CMP slurry flow 1210. A detector 1220 detects radiation 1212c and generates signals indicative of transmission of radiation 1212b through sample and flow 1208, 1210. These signals are interpreted by processor 1220, e.g., a computer, to determine a transmission value as a function of wavelength (or waveband). By way of example, if source 1214 generates radiation 1212a that is filtered by filter 1216a to 2.5 microns +/−0.2 micron, then detector 1220a can correspond to a near infrared detector, e.g., InGaAs, to detect transmission of radiation 1212c through sample and flow 1208, 1210. Transmission is determined by computer 1220 and associated with "2.5 microns." At times, multiple detectors 1220a, 1220b . . . 1220n are required to detect all the wavelengths of interest from sources 1214a, 1214b . . . 1214n. Detectors 1220 can be inserted within system 1200, as needed, to measure appropriate wavelengths, or an appropriate optical technique such as illustrated in FIG. 1 can be used to achieve the same function.

Different slurry supplies 1204a, 1204b . . . 1204m can also be coupled to system 1200 in a manufacturing process; and each CMP slurry 1202a, 1202b . . . 1202m can then be coupled to sample cell 1208 as required through appropriate flow pathways 1206. Alternative sample cells 1208a, 1208b . . . 1208q can be used in system 1200, as needed, to acquire appropriate optical path lengths corresponding to enhanced detection of radiation 1212b through sample cell and flow 1208, 1210. As before, sample cells 1208 can be switched into system 1200 manually, or mechanically, or an optical configuration such as FIG. 1 can be used to achieve the same function (i.e., multiple samples are mounted within system 1200 and radiation of the appropriate wavelength is re-routed to the correct sample cell 1208 through different optical paths and beam splitters).

CMP slurry from flow 1210 leaves sample cell 1208 along slurry line 1222, which couples to semiconductor manufacturing process 1224. When system 1200 detects bad CMP slurry, as discussed herein (e.g., slurry with a particle distribution extending beyond a desirable range), then processor 1220 sends a warning signal to warning device 1226, e.g., a light, audible alarm or other device (e.g., a computer) coupled or proximate to manufacturing process 1224. In this manner, manufacturing process 1224 is informed, in real time, of CMP slurry quality control issues which can damage and destroy semiconductor surfaces used in integrated circuit devices.

Figure 12A:
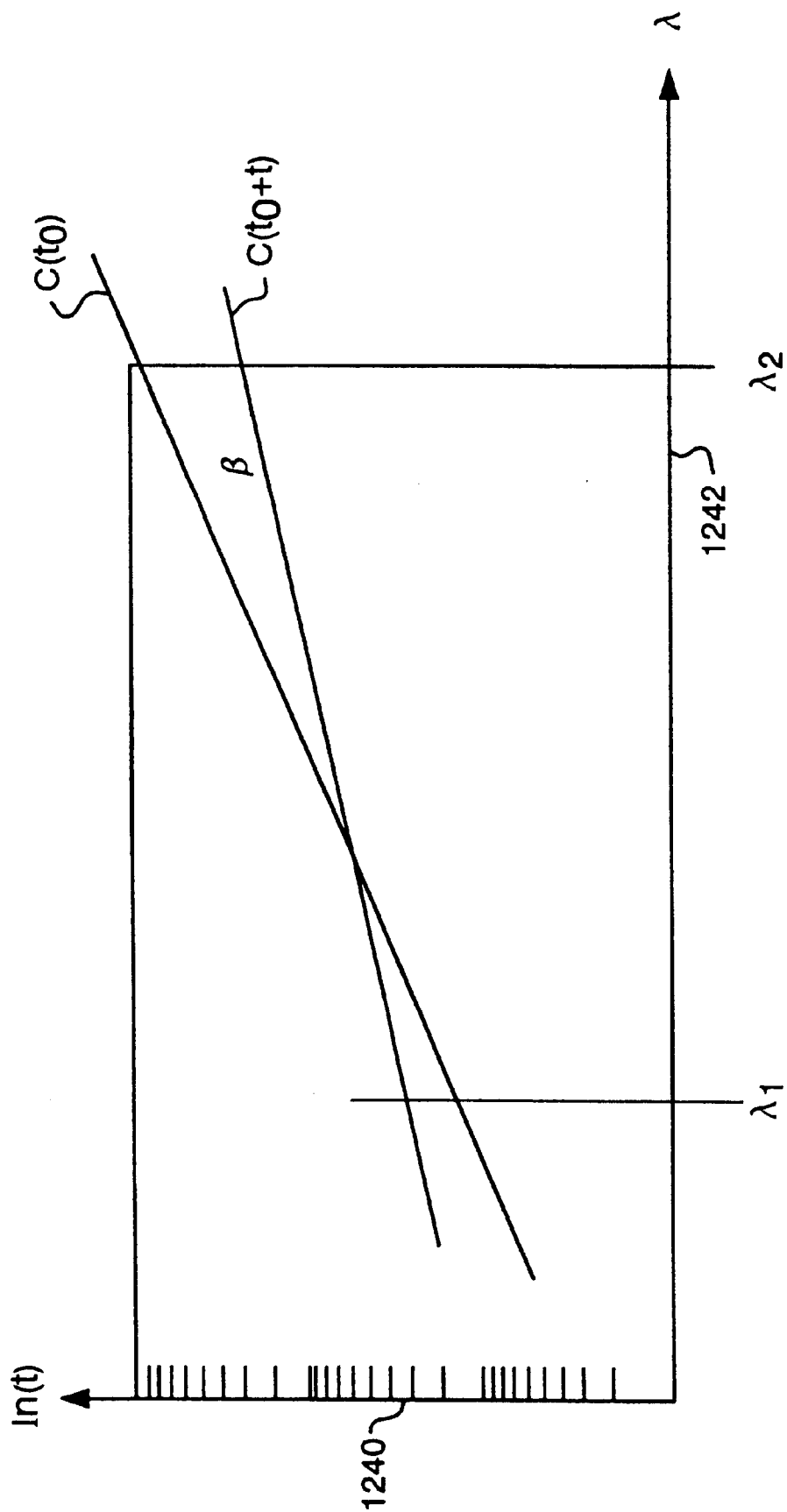
FIG. 12A illustrates representative transmission versus wavelength curves generated in accord with the invention to detect "good" versus "bad" CMP slurries during quality control.

Transmission values determined by system 1200 are preferably plotted with respect to wavelength, such as illustrated in FIG. 12A. Specifically, the natural log of transmission values (ln(t), axis 1240) is plotted against wavelength ($\lambda$, axis 1242), as shown. Accordingly, the slope of a line C which approximates ln(transmission($\lambda$)) at time to may be determined, such as line C($t_0$). At a later time t, line C may for example be plotted as C($t_0$+t), indicating a change in the slope of ln(transmission($\lambda$)). When the slope of line C changes by a sufficient amount, represented by angle $\beta$, determined empirically or by another measure, then the particle distribution sizes within the CMP slurry have changed and system 1200 sends a warning to manufacturing process 1224. FIG. 12A also illustrates wavelength measurement points $\lambda_1$, $\lambda_2$ used to determine the slope of line C, as known in the art. Each $\lambda$ sample corresponds to a measurement point corresponding radiation passed through filter 1216, for example. Each waveband a is centered about a wavelength $\lambda$ such that $\Delta\lambda/\lambda$ is less than approximately 5%. For example, for $\lambda$=2.5 microns, a corresponds to 1bout 0.13 micron.

The function of source(s) 1214 and filter(s) 1216 can be replaced by laser diodes, if desired. Alternatively, filter(s) 1216 can be replaced by appropriate dispersive elements (e.g., gratings) located with detector(s) 1220, such as discussed in FIG. 1.

Processor 1220*a* preferably includes solid state memory to store one or more "reference transmission" data corresponding to a preferred transmission vs. wavelength curve, or ln(t) vs. $\lambda$ data, for a known CMP slurry with acceptable particle size distribution. The reference transmission data further includes an acceptable variance of that data from optimal where CMP slurry is deemed "acceptable." Accordingly, in this embodiment, system 1200 evaluates transmission data from flow 1210 in real time and compares that data to reference transmission data in memory 1220*a*, and generates a warning when the real time data exceeds the allowed variance, indicating an "unacceptable" CMP slurry. Memory 1220*a* can further include an array of curves or ln(t) vs. $\lambda$ data corresponding to each CMP slurry 1202*a*, 1202*b* . . . 1202*m*, as appropriate, such that system 1200 can operate with multiple CMP slurries used in manufacturing process 1224. A user can select which reference transmission data to use at any one time through a user interface (e.g., a keyboard) at processor 1220.

Figure 6:
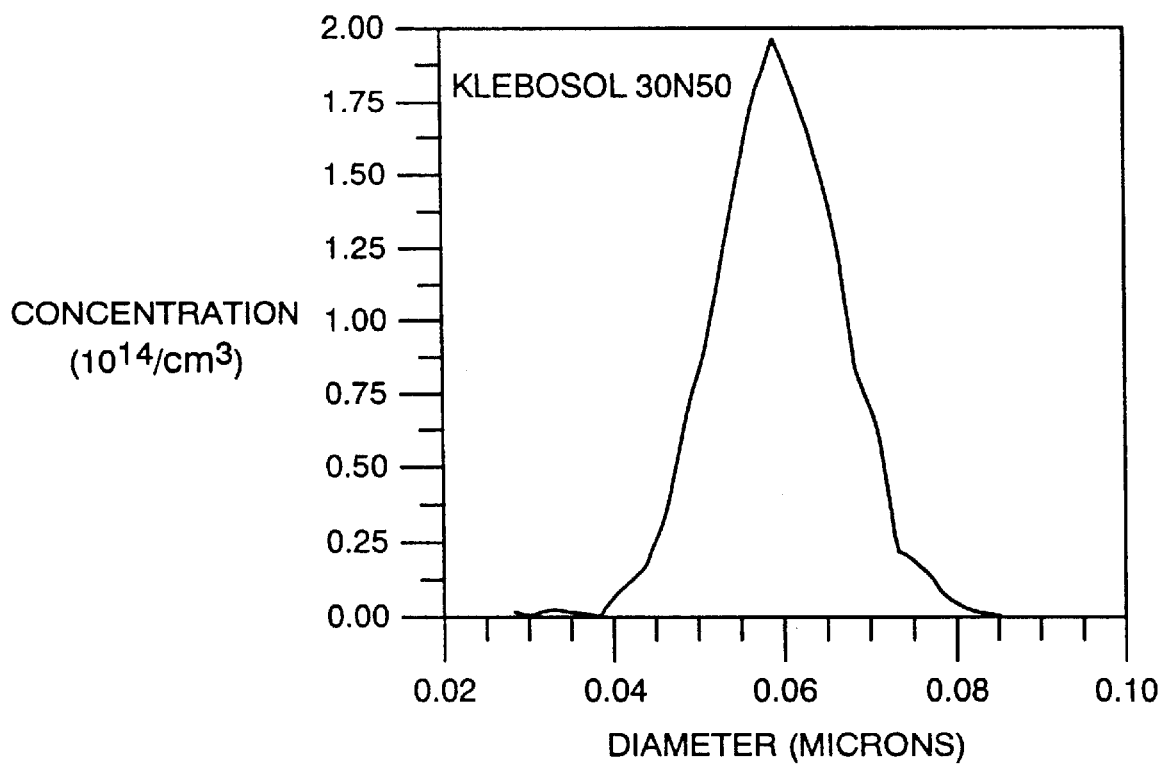
FIG. 6 depicts a manufacturer's scanning electron microscope-based particle size distribution corresponding to the spectral transmission data of FIG. 5.

Measuring particle size distributions within CMP slurry flow 1210 is also a feature of the invention. Typically, these distributions are centered about a particular particle size, e.g., 0.06 micron, as shown in FIG. 6. Other suitable center particle sizes in accord with the invention are between about 0.3 and 1.0 micron, though particle size distributions centered about a value between 0.1 and 0.3 micron, or 1.0 and 10 microns, are also envisioned and within the scope of the invention. Typically, the diameter of flow 1210 is approximately 100 microns for near-infrared wavelengths. Smaller flow diameters, i.e., down to 50 microns or smaller, are also envisioned, as are larger flow diameters up to approximately 2000 microns, all within the scope of the invention.

Figure 12B:
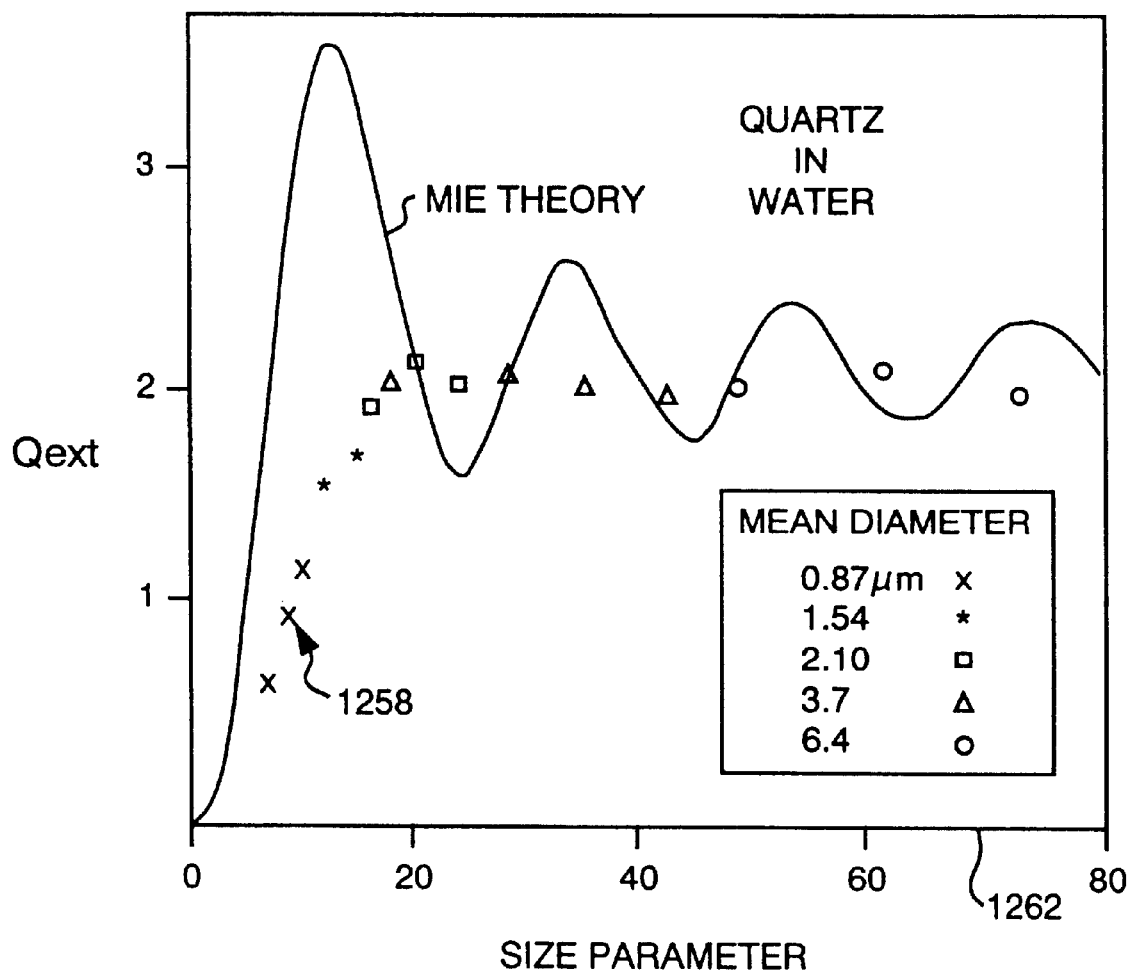
FIG. 12B depicts representative extinction versus particle size data used to evaluate particle sizes in real time in a manufacturing process, in accord with the invention.

Mie theory can be used to determine particle size distributions in CMP slurry flow 1210. Alternatively, an empirical curve of extinction efficiency QE versus particle size diameter D is developed and stored in memory 1220*a*; and that empirical curve is compared to data obtained by system 1200 in real time. The particle size function preferably corresponds to $\pi D/\lambda$, where $\lambda$ corresponds to the waveband of measurement. FIG. 12B illustrates exemplary $Q_E$ versus $\pi D/\lambda$ empirical data 1258 for different particle sizes, with QE on vertical axis 1260 and size parameter $\pi D/\lambda$ on horizontal axis 1262. Bohren et al., *Absorption and Scattering of Light by Small Particles*, John Wiley & Sons, p. 319 (1983). To determine particle size D, $Q_E$ is calculated directly as a function of transmission t, discussed above, and multiplied by $\lambda/\pi$.

Figure 13:
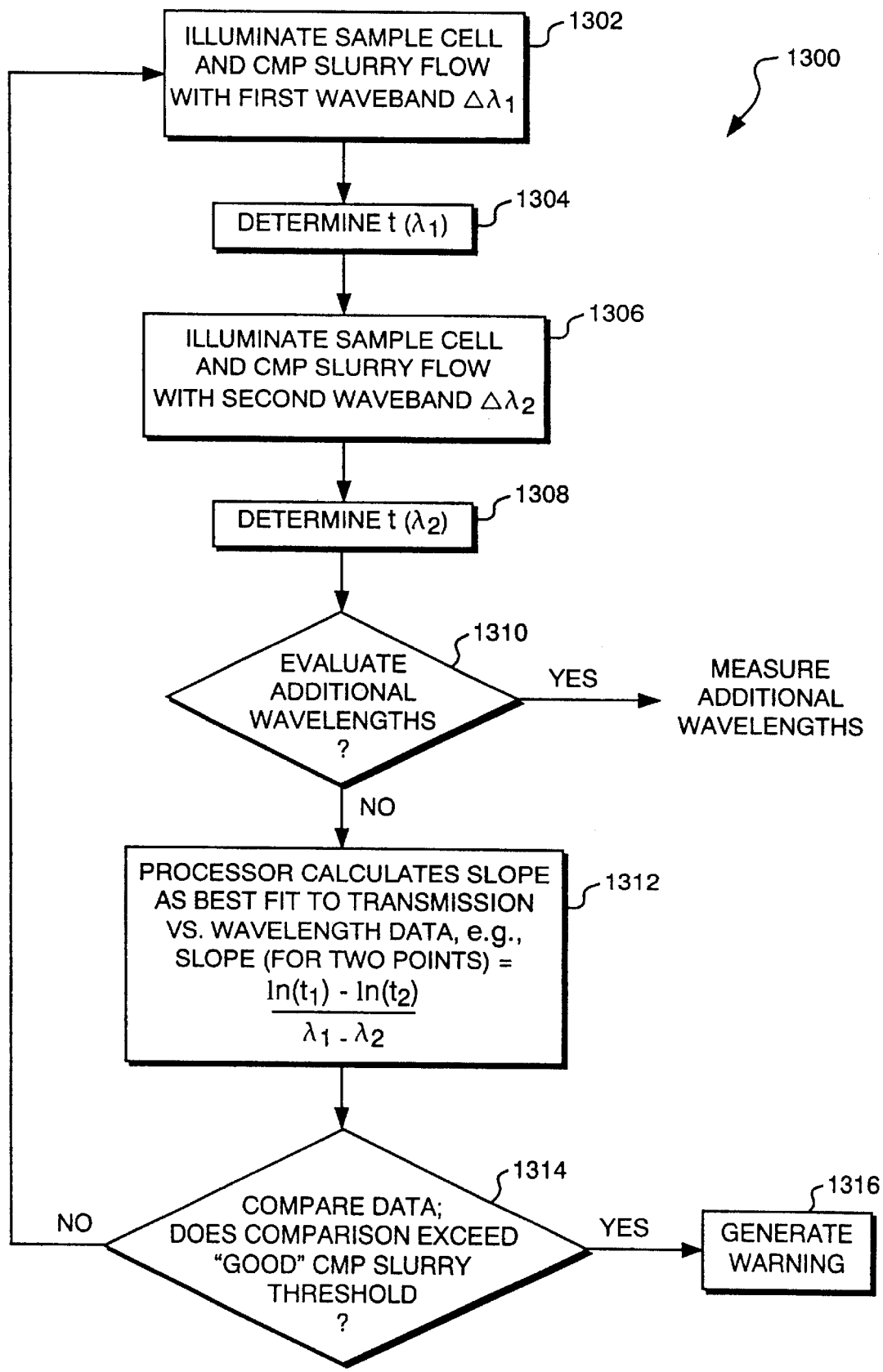
FIG. 13 schematically illustrates a process flow of the invention for detecting and informing users of unacceptable CMP slurry particulate distributions, in near real-time.

FIG. 13 shows a process flow 1300 of the invention for detecting CMP slurry quality and/or particle size distribution. Process flow 1300 is representative for use of a system of the invention, such as illustrated in FIGS. 1 or 12. In process step 1302, the sample cell and CMP slurry flow is illuminated by radiation at a first waveband $\Delta\lambda_1$, e.g., 0.08 micron centered about 1.7 microns ($\lambda_1$). The system detector and processor then measure and determine a transmission value for $\lambda_1$, in process step 1304. In process step 1306, the sample cell and CMP slurry flow is illuminated by radiation at a second waveband $\Delta\lambda_2$, e.g., 0.03 micron centered about 0.6 micron ($\lambda_2$). The system detector and processor then measure and determine a transmission value for $\lambda_2$, in process step 1308. The systems and methods of the invention can detect further transmission values for other wavelengths and wavebands, as desired at step 1310, or calculate the slope of the transmission versus wavelength slope as set forth in step 1312. In step 1314, the slope measured in step 1312 is measured against a reference slope stored in system memory, or alternatively the current slope is compared to prior slope information, to evaluate change in the CMP slurry particle distribution. If the slope exceeds a predetermined amount from prior slope information, or from reference slope transmission data, then a warning is generated in step 1316. Otherwise, a next set of transmission data is taken in steps 1302–1308 to evaluate CMP slurry quality over time.

Figure 14:
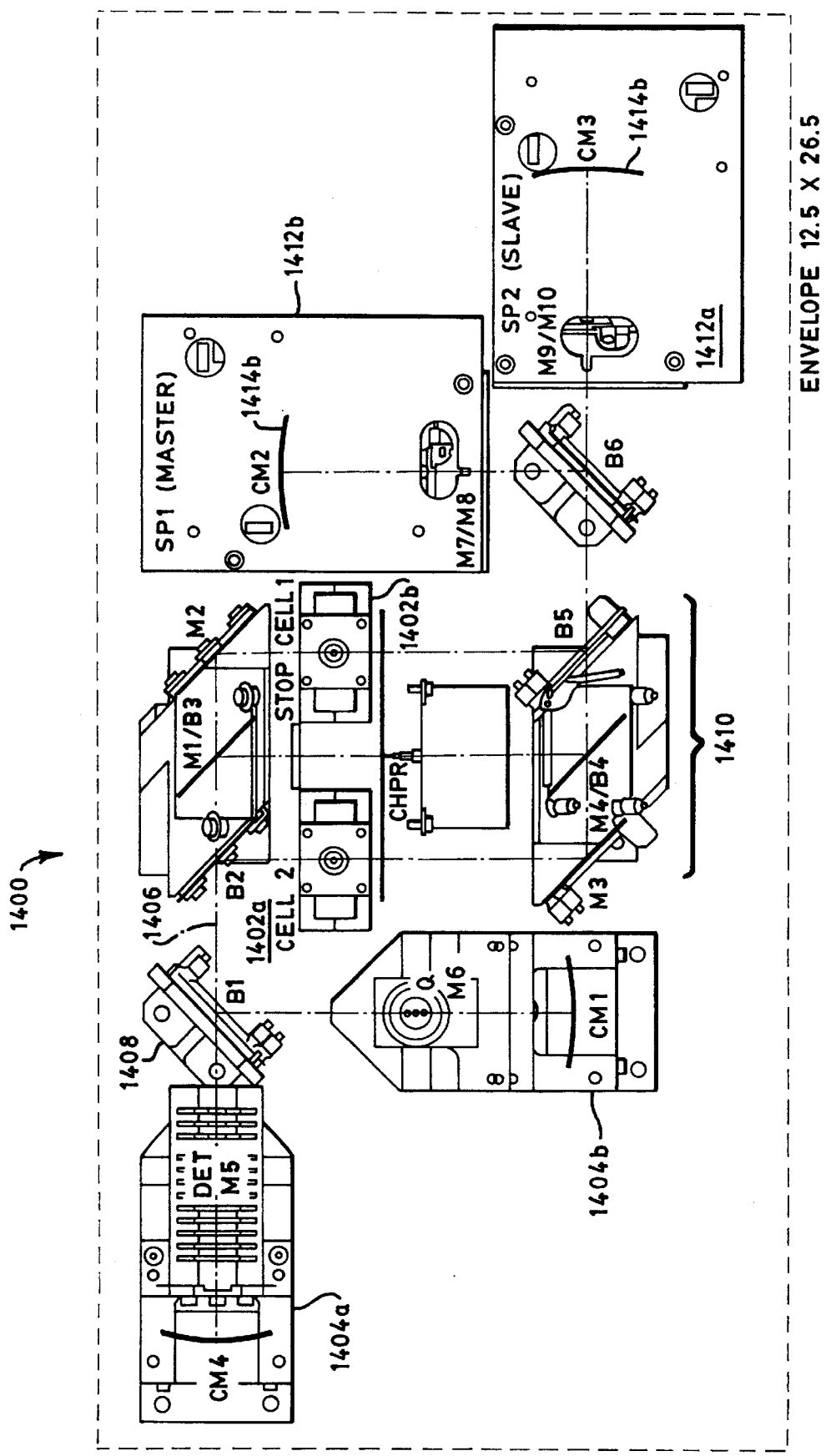
FIG. 14 schematically shows one CMP slurry quality control process and particle distribution measuring system constructed according to the invention.

FIG. 14 depicts one CMP slurry particle measuring and quality control system 1400 constructed according to the invention. Two sample cells 1402*a*, 1402*b* (e.g., similar to sample cells 154, 162, FIG. 1) are used to extend the spectral range within which one obtains high accuracy transmission measurements to determine CMP slurry quality and/or particle size. Sources 1404*a*, 1404*b* generate radiation beam 1406 in different wavebands through beam splitter 1408. Other beam splitters and optics 1410 translate beam 1406 to appropriate grating spectrometers 1412*a*, 1412*b*, each with a mirror assemblies 1414*a*, 1414*b* used to isolate the desired waveband of interest.

The invention thus attains the objects set forth above, among those apparent from the preceding description. Since certain changes may be made in the above methods and systems without departing from the scope of the invention, it is intended that all matter contained in the above description or shown in the accompanying drawing be interpreted as illustrative and not in a limiting sense. It is also to be understood that the following claims are to cover all generic and specific features of the invention described herein, and all statements of the scope of the invention which, as a matter of language, might be said to fall there between.

Having described the invention, what is claimed is:

1. A quality control process for detecting physical and/or chemical changes in a CMP slurry, comprising the steps of:

transmitting radiation through a flow of an undiluted optically dense slurry as used in a chemical mechanical planarization (CMP) process, the radiation having one or more wavelengths;

determining transmission of the transmitted radiation at each of the wavelengths; and monitoring transmission, over time, to detect physical and/or chemical changes of the CMP slurry.

2. A process of claim 1, further comprising determining a slope of transmission as a function of the wavelengths.

3. A process of claim 1, further comprising the step of detecting changes in the particle size distribution of the CMP slurry.

4. A process of claim 3, further comprising the step of determining a change in the slope, over time, the change in slope indicating change in the particle size distribution.

5. A process of claim 3, further comprising determining a slope of a logarithmic of transmission.

6. A process of claim 1, further comprising the step of determining a slope of a logarithmic of transmission as a function of the wavelengths.

7. A process of claim 6, further comprising the step of determining a change in the logarithmic slope, over time, the change in the slope indicating change in a particle size distribution of the CMP slurry independent from a change in particle concentration.

8. A process of claim 1, further comprising the step of detecting changes in the particle size distribution of the CMP slurry wherein the particle size distribution corresponds to a value between about 0.03 and 1.0 micron.

9. A process of claim 1, further comprising the step of detecting changes in the particle size distribution of the CMP slurry wherein the particle size distribution corresponds to a value above about one micron.

10. A process of claim 1, wherein the step of transmitting the radiation comprises transmitting the radiation through the flow having a diameter of about 100 microns.

11. A process of claim 1, wherein the step of transmitting the radiation comprises transmitting the radiation through the flow having a diameter of between about 100–2000 microns.

12. A process of claim 1, wherein the step of transmitting the radiation comprises transmitting the radiation through a sample cell selected on the basis of desired accuracy.

13. A process of claim 12, further comprising selecting a sample cell defining a flow diameter of about 100 microns.

14. A process of claim 12, further comprising selecting a sample cell defining a flow diameter of between about 100–2000 microns.

15. A process of claim 1, wherein the step of determining transmission comprises determining transmission to an accuracy of at least about 1%.

16. A process of claim 1, wherein the step of transmitting comprises utilizing a grating to select the wavelengths of the radiation.

17. A process of claim 1, wherein the step of transmitting comprises using a laser.

18. A process of claim 1, wherein the step of transmitting comprises utilizing at least two filters to select the wavelengths.

19. A process of claim 1, further comprising generating a warning corresponding to the changes.

20. A process of claim 1, further comprising the steps of detecting changes in the particle size distribution of the CMP slurry and of comparing the transmission to a reference transmission indicative of a preferred particle size distribution within the flow.

21. A process of claim 20, further comprising the step of storing the reference transmission in memory.

22. A process of claim 1, further comprising the steps of
(a) detecting changes in the particle size distribution of the CMP slurry
(b) storing a plurality of reference transmissions, each reference transmission corresponding to a particular CMP slurry flow and particle distribution, and (c) selecting one reference transmission and comparing the transmission to the selected reference transmission.

23. A process of claim 1, further comprising utilizing Mie theory to calculate particle sizes within the CMP slurry.

24. A process of claim 1, further comprising comparing transmission information with an empirical curve of extinction efficiency versus particle size diameter to determine particle sizes within the CMP slurry.

25. A process of claim 24, wherein the particle size diameter comprises a function of (pi) D/ lambda, where D is the particle size diameter and lambda corresponds to wavelength associated with the transmission.

26. A system for evaluating chemical mechanical planarization (CMP) slurry quality in a process, comprising:

a light source generating a beam of electromagnetic radiation for transmission through a flow of an undiluted optically dense slurry as used in a CMP process;

a spectral discriminator for isolating at least two wavelength bands of the radiation prior to transmission of the radiation through the flow;

a detector for detecting radiation transmitted through the flow; and a processor for evaluating transmission of the wavelength bands through the flow to determine physical and/or chemical changes of the CMP slurry.

27. A system of claim 26, wherein the discriminator comprises two wavelength bandpass filters.

28. A system of claim 26, wherein the discriminator comprises a filter wheel.

29. A system of claim 26, wherein the discriminator is selected from the group consisting essentially of a laser and a grating.

30. A system of claim 26, wherein the processor comprises a computer.

31. A system of claim 26, further comprising memory, coupled to the processor, for storing one or more reference transmissions, each reference transmission corresponding to a particular CMP slurry flow and particle size distribution, the processor selecting one reference transmission and comparing the transmission to the selected reference transmission to detect changes in the particle size distribution.

32. A system of claim 26, further comprising memory, coupled to the processor, for storing data indicative of extinction efficiency as a function of particle size diameter, the processor comparing the transmission to the data to determine particle sizes within the CMP slurry.

33. A system of claim 26, wherein the processor comprises processing means to calculate a logarithm of transmission at each wavelength band and to determine a change in slope of logarithmic transmission versus wavelength band to detect changes in particle size distribution of the CMP slurry independently from changes in particle concentration.

* * * * *